United States Patent [19]

Forrest et al.

[11] Patent Number: 5,149,630
[45] Date of Patent: Sep. 22, 1992

[54] METHODS OF ASSAY

[76] Inventors: Gordon C. Forrest, Braemore, High Park Avenue, East Horsley, Surrey KT24 5DP; Hugh A. O. Hill, 9 Clover Close, Oxford; Simon J. Rattle, 29, Lower Street, Quainton, Buckinghamshire, HP22 4BL; Grenville A. Robinson, 23 Burnham Way, Ealing, London W13 9YF, all of England

[21] Appl. No.: 157,100

[22] Filed: Feb. 9, 1988

Related U.S. Application Data

[63] Continuation of Ser. No. 694,923, Jan. 25, 1985, abandoned.

[30] Foreign Application Priority Data

Jan. 26, 1984 [GB] United Kingdom ............... 8402058

[51] Int. Cl.$^5$ .............................. G01N 33/536
[52] U.S. Cl. .......................... 435/7.9; 204/403; 436/806; 436/808; 435/25; 435/810; 435/817; 435/14
[58] Field of Search ............. 435/7, 14, 810, 25, 435/817; 436/806, 808; 204/403

[56] References Cited

U.S. PATENT DOCUMENTS

| | | | |
|---|---|---|---|
| 4,081,334 | 3/1978 | Suzuki | 204/403 |
| 4,340,448 | 7/1982 | Schiller | 435/817 |
| 4,391,904 | 7/1983 | Litman | 435/7 |
| 4,545,382 | 10/1985 | Higgins | 204/403 |
| 4,600,690 | 7/1986 | Karmen | 435/7 |
| 4,711,245 | 12/1987 | Higgins | 435/25 |
| 4,758,323 | 7/1988 | Davis et al. | 204/403 |

OTHER PUBLICATIONS

Itagaki Chem. Pharm. Bull. 31(4) pp. 1283-1288 (1983).
Eggers Clin. Chem. 28(9), pp. 1848-1851 (1982).
Alexander Anal. Chem 54, pp. 68-71 (1982).
Yolken Reviews of Infections Diseases 4(1), pp. 35-42 (1982).
"Direct electrochemical reduction of ferrodoxin promoted by Mg$^{2+}$" by F. A. Armstrong et al., FEBS Letters, vol. 145, No. 2.
"Direct Electrochemistry of Redox Proteins at Pyrolytic Graphite Electrodes" by F. A. Armstrong et al., J. Am. Chem. Soc. 1984, 106, 921-923.
"Electrochemistry of Cytochrome c. Comparison of the Electron Transfer . . . " by J. S. Miller et al., 1979, Journal of American Chemical Society, pp. 7113-7114.
"Surface Modifiers For The Promotion Of Direct Electrochemistry of Cytochrome c" by P. M. Allen et al., J. Electroanal. Chem. 178 (1984) 69-86.
Maggio "Enzyme-Immunoassay", ed. Edward T. Maggio, CRC Press, pp. 53-65 (1980).

*Primary Examiner*—Esther L. Kepplinger
*Assistant Examiner*—Christopher L. Chin
*Attorney, Agent, or Firm*—Ostrolenk, Faber, Gerb & Soffen

[57] ABSTRACT

An electrochemical specific binding assay of a ligand (e.g., antigen, hapten or antibody) wherein at least one of the components is enzyme-labelled, and which includes the step of determining the extent to which the transfer of electrons between the enzyme substrate and an electrode, associated with the substrate reaction, is perturbed by complex formation or by displacement of any ligand complex relative to unbound enzyme-labelled component.

The electron transfer is aided by electron-transfer mediators which can accept electrons from the enzyme and donate them to the electrode or vice versa (e.g. ferrocene) or by electron-transfer promoters which retain the enzyme in close proximity with the electrode without themselves taking up a formal charge.

The electrochemical apparatus will typically comprise two or three electrodes, including one working electrode onto which components may advantageously be immobilized.

The use of direct electrochemical measurement of the enzyme label avoids the errors and inconvenience of the known indirect measurement techniques.

22 Claims, 12 Drawing Sheets

METHODS OF ASSAY

This is a continuation of application Ser. No. 694,923 filed on Jan. 25, 1985, now abandoned.

METHODS OF ASSAY

The present invention relates to methods of assaying one of a pair of specific binding partners, and to apparatus and kits of reagents for carrying out these methods.

There is today a great need for rapid and accurate methods of assaying biologically active substances (which may be at low concentrations), particularly in body fluids such as blood, saliva or urine. A wide variety of medical conditions such as pregnancy, drug overdose, metabolic birth defects, hormonal disorders and diabetes can be diagnosed using such assay techniques.

Many assay methods rely on the formation of a complex between the species under assay (hereinafter called "ligand") and another species to which it will bind specifically (hereinafter called "specific binding partner"). The extent of complex formation is a function of the amount of the ligand present.

The assay of ligand is determined by monitoring the extent of complex formation, for example by the use of chemical or biochemical labels. Several methods of labelling have been employed, for example using radioisotopic, fluorescent or bioluminescent species, spin-labelling or enzyme labelling.

There are serious disadvantages to the use of radioactive labels. They have limited shelf-life due to spontaneous decay, necessitating frequent recalibration of the equipment, and their use requires adherence to strict safety precautions and is subject to legal regulation. These disadvantages inevitably lead to higher costs and the necessity for high standards of sophistication of equipment, laboratory facilities and personnel.

In view of such disadvantages associated with radioactive labels, the use of enzymes represents potentially an extremely valuable labelling technique.

There are two categories of assays employing enzyme labels, designated respectively 'heterogeneous' and 'homogeneous'. In heterogeneous techniques, the activity of the enzyme label towards its substrate remains constant, irrespective of whether or not the labelled reagent becomes bound to its specific counterpart in the complexing reaction. In such techniques, it is therefore necessary to separate the reactants into two fractions before determining the proportion of label in either the complexed or uncomplexed phase. In homogeneous techniques, the enzyme label behaves differently depending on whether or not the reagent becomes bound to its specific counterpart in the complexing reaction, and no separation stage is required. By measuring the change in activity of the enzyme label towards its substrate as a result of complexing, the assay of the ligand may be determined.

In general the heterogeneous technique is the more sensitive (having comparable sensitivity to assays using radioisotopic labels) while the homogeneous technique is the simpler and the quicker (being considerably superior in these respects to radioisotopic labelling). Homogeneous enzyme-labelled assay methods are particularly suitable for automation. In terms of the lack of legal restrictions, the relatively low operating costs and expertise required and the safety and stability of the reagents, both the homogeneous and the heterogeneous techniques are considerably superior to assay methods using radioisotopic labels.

Hitherto, however, only indirect methods of monitoring the enzyme label have been used. Thus, for example, the appearance of the product of the enzyme-catalysed reaction has been measured by spectrophotometry (by virtue of the generation of a coloured species either as a result of the substrate reaction or as a result of a secondary reaction in which the product of the substrate reaction reacts with a chromogen, optionally in the presence of a second enzyme, the enzyme activity being determined by the change in the colour of the solution), by nephelometry (in which the product causes the solution to become turbid, the degree of turbidity being related to the enzyme activity) by fluorimetry or radiometry (in which the appearance of a fluorescent or radioactive marker in the product is monitored) or by measuring the change in the pH of the solution. Alternatively, the consumption of the reactants has been measured, for example by gas analysis in the case of oxidation reactions in which atmospheric oxygen is a reactant.

Thus, for example, in assays using the enzyme label glucose oxidase (GOD) (E.C.1.1.3.4), which catalyses the oxidation of β-D-glucose to D-glucono δ-lactone (with hydrogen peroxide as a byproduct), the label has been monitored by following the reduction of the hydrogen peroxide in the presence of horseradish peroxidase and a chromogen according to the following scheme

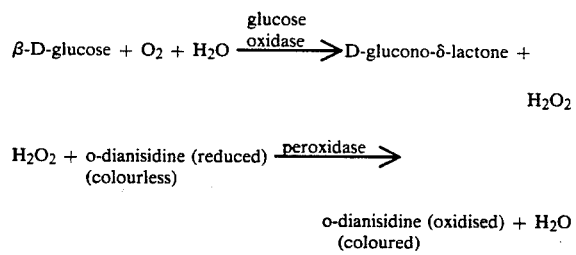

Such indirect monitoring techniques lack the high degree of sensitivity and specificity required for modern assay work. This may be due to the fact that neither the primary nor the secondary reaction is 100% quantitative or there may be inaccuracy in end-point assessment. The use of radioactive labels presents the usual problems of safety and short shelf-life of the reagents. The chromogens used in spectrophotometric techniques are often carcinogenic.

It is one of the objects of the present invention to overcome these disadvantages to the use of enzyme labels and to provide a sensitive, specific and convenient assay method in which the enzyme label is monitored directly.

BRIEF DESCRIPTION OF THE DRAWINGS

FIG. 1b shows a circuit arrangement for the cell of FIG. 1a;

Figure 1A:
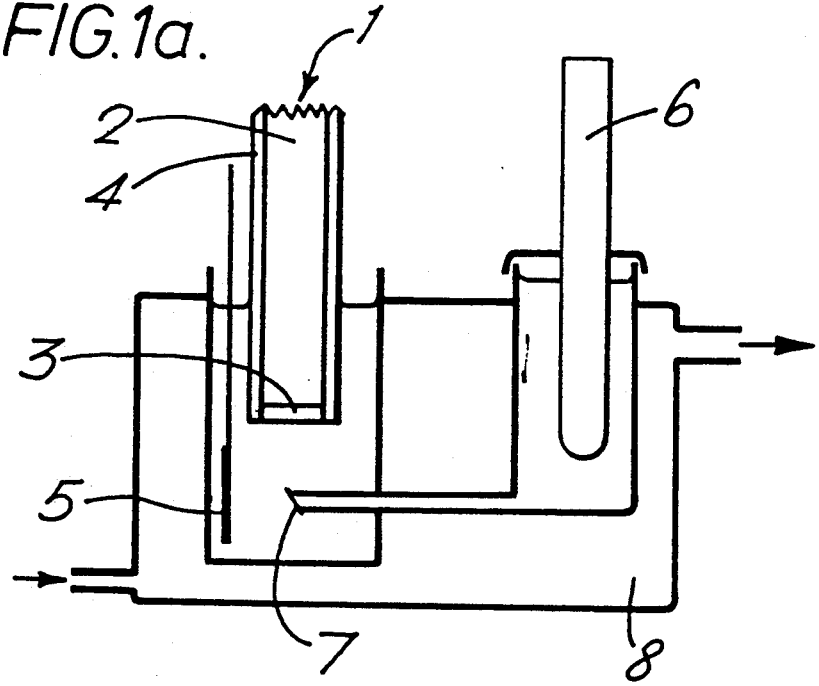
FIG. 1a shows an electrochemical cell using a pyrolytic graphite working electrode.

We have now discovered that electrochemical techniques can be applied to enzyme-labelled assay methods, to provide means for directly monitoring the activity of the enzyme label.

Thus, in its broadest aspect, the invention provides a method of assay of a ligand in a sample using an electrochemical apparatus containing an electrode and components comprising (a) the sample, (b) a specific binding partner to the ligand, (c) if desired, at least one further reagent selected from ligand analogues (as herein defined) and specific binding partners, at least one of components (b) and, if present, (c) being enzyme-labelled, (d) a substrate for the enzyme, and (e) a chemical species capable of aiding the transfer of electrons from the substrate to the electrode via the enzyme resulting from the oxidation of the substrate, or the transfer of electrons from the electrode to the substrate via the enzyme permitting reduction of the substrate, which method includes the step of determining whether, and if desired the extent to which, the said transfer of electrons is perturbed by complex formation and/or by controlled external influences.

The assay can be completed from the determined perturbation with reference to calibration data.

The term "ligand analogue" used herein refers to a species capable of complexing with the same specific binding partner as the ligand under assay, and includes inter alia within its scope a known quantity of the ligand species under assay.

The term "enzyme-labelled" used herein refers to the attachment of an enzyme (which term includes both true enzymes and apoenzymes which may become activated in the presence of a cofactor) to at least one of the reagents comprising components (b) and (c). Preferred enzymes are the so-called oxidoreductases, particularly, but not exclusively, flavo- and quino-protein enzymes, e.g. glucose oxidase, glucose dehydrogenase or methanol dehydrogenase. As an apoenzyme, for example, apoglucose oxidase may be used.

The enzyme may be attached to components (b) and (c) by any of the conventional methods for coupling to other substances, for example, employing covalent or non-covalent bonding using bifunctional reagents such as glutaraldehyde, periodate, N,N'-o-phenylenedimaleimide, m-maleimidobenzoyl-N-hydroxysuccinimide ester, succinic anhydride, a mixed anhydride, or a carbodiimide. Alternatively, cross-linking or the formation of, for example, an avidin/biotin or protein A/IgG complex may be used. The site of attachment will generally be remote from the active site of the enzyme so that the enzyme activity is not impaired. Furthermore, attachment of the enzyme should not affect the specific binding characteristics of components (b) and (c).

The chemical species of component (e) may, for example, comprise an electron transfer mediator which can accept electrons from the enzyme and donate them to the electrode (during substrate oxidation) or can accept electrons from the electrode and donate them to the enzyme (during substrate reduction). The mediator may, for example, be selected from the following:

(i) a polyviologen such as, for example, a compound of formula

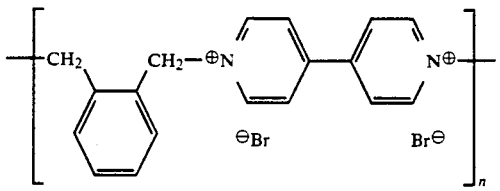

and derivatives thereof, e.g. side-chain alkyl derivatives, the preparation of which is described in Polymer Letters 9 pp 289–295 (1971), (ii) a low molecular weight compound selected from chloranils, fluoranils and bromanils (e.g. o-chloranil), (iii) ferrocene (bis-$\eta^5$-cyclopentadienyl iron (II)) or a derivative thereof [including e.g. functionalised derivatives such as ferrocene monocarboxylic acid (FMCA), dimethylaminomethyl ferrocene, polymeric forms ('polyferrocenes') such as (ferrocene)$_4$ or polyvinyl ferrocene and 'boron tetraferrocene' (B(ferrocene)$_4$)], (iv) compounds of biological origin possessing suitable enzyme compatability, e.g. Vitamin K, (v) N,N,N',N'-tetramethyl-4-phenylenediamine, and (vi) derivatives of phenazine methosulphate or phenazine ethosulphate.

Mediators may interact with the enzyme at a site remote from or near to the active site for the substrate reaction, and remote from or near to the site of attachment of the reagents (b) and (c). Proximity of the site of enzyme-mediator interaction to the site of attachment of the reagents can result in prevention of electron transfer between the enzyme and the mediator on formation of the complex between the ligand or ligand analogue and the specific binding partner, permitting a homogeneous assay method, as described below.

The preferred electron transfer mediators are ferrocene and functionalised derivatives thereof. These compounds are desirable for this purpose because they are relatively cheap, stable, non-toxic, and provide an easily electrochemically reversible system which in its reduced $Fe^{II}$ state is not susceptible to oxidation by oxygen in the atmosphere.

Electron transfer mediators may require functionalisation in order to permit successful interaction with the electrode and/or the enzyme or to improve the electrochemical or other properties of the mediator. For example, the redox potential of ferrocene is +422 mV vs NHE. By introducing functional groups on to the ring system, this figure can be varied between +300 and +650 mV. Moreover, the water-solubility of carboxyl-substituted ferrocenes is greater than that of the parent compound (see, e.g. R. Szentrimay, 1977 Amer. Chem. Soc. Symposium Series, 38, 154).

Thus, for example, in the case of ferrocene, it may be necessary to modify the ferrocene complex by providing one or both of the cyclopentadienyl groups with one or more side chains, e.g. of the formula

—CHO

—$(CH_2)_n$COOH or

—$(CH_2)_m$$NR^1R^2$ where n and m may be e.g. from 0 to 6 and $R^1$ and $R^2$, which may be the same or different, each represents hydrogen or an alkyl group containing from 1 to 4 carbon atoms (e.g. methyl). Additional functional groups may be incorporated into the side chain, typically those groups used in the chemical modification of proteins, for example mercuric chloride, precursors of nitrenes and carbenes, diazo or iodide groups. Similar functionalisation may be desirable when mediators other than ferrocene are used.

Alternatively, the chemical species of component (e) may comprise an electrode-immobilised electron transfer promoter which, unlike the mediators described above, does not take up a formal charge during electron transfer, but aids the flow of electrons by retaining the enzyme in close proximity with the electrode., The promoter may, for example, be a magnesium ion or 4,4'-bipyridyl, the latter being particularly suitable for use with laccase or superoxide dismutase and a gold working electrode.

The interaction between the component (e) and the enzyme may thus take the form of chemical bonding e.g. in ways analagous to the bonding of the enzyme label to components (b) and, if present (c) as described above, or may take the form of non-chemical bonding or non-bonding interaction.

The working electrode from which the electrochemical readings will be taken will preferably be solid and have a electrically conductive working surface of e.g. carbon (preferably graphite e.g. pyrolytic graphite), or metal e.g. silver, gold or platinum. If the electrode is of carbon, it may be present as a pre-formed rod or as an electrode shape made up of a paste of carbon particles. The nature of the surface of the electrode is usually important—if metal, the surface can be roughened; if solid carbon, the surface can be previously heat-treated in an oven with oxygen excess or oxidised electrochemically.

In addition to the working electrode from which the electrochemical readings will be taken, the apparatus will comprise an auxiliary (counter) electrode and optionally a reference electrode, the electrodes being used in conjunction with a potentiostat and a sensitive current meter. The apparatus preferably contains an aqueous assay medium comprising inter alia pH buffer. Means may be provided for incubating the assay medium at any desired temperature. A suitable electrochemical apparatus is illustrated in vertical cross-section in FIG. 1(a) of the accompanying drawings. The working electrode 1 is composed of an elongate core 2 of steel tipped with a working surface 3 of pyrolytic graphite and having a coating 4 of epoxy resin. The auxiliary (counter) electrode 5 is of platinum. A calomel reference electrode 6 is shown, connected to the cell via a luggin capillary 7. The cell and reference electrode are enclosed in a water jacket 8.

Figure 1B:
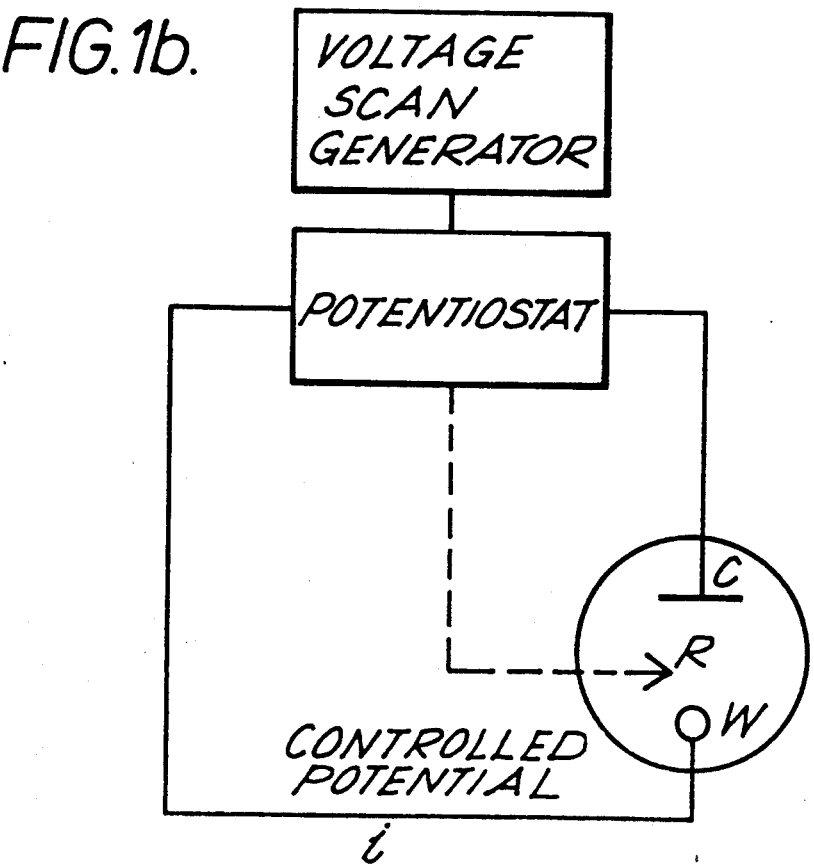

A variety of electrochemical methods exploiting any two of the three parameters potential (E), current (i) and time (t) may be used to measure the electrochemical characteristics of the components. For example, electrochemical measurements can be made using differential pulse voltammetry, cyclic voltammetry or square-ware voltammetry. When cyclic voltammetry is used, a circuit such as, for example, that shown schematically in FIG. 1b of the accompanying drawings may be employed. In this Figure, C represents the auxiliary (counter) electrode, W the working electrode and R the reference electrode. This circuit may conveniently be used in conjunction with apparatus of the type shown in FIG. 1a, the electrochemical current i being measured using a potentiostat.

In homogeneous assay systems the formation of the complex between the ligand and the specific binding partner or, in the case of competitive assays, between the ligand analogue and the specific binding partner, may cause a change in the ability of electrons to flow from the enzyme to the electrode and vice versa. This may, for example result from:

1. prevention of the substrate entering, or product leaving, the active site of the enzyme on formation of the complex;

2. alteration of the conformation of the enzyme by the formation of the complex such that the enzyme is incapable of oxidising or reducing its substrate despite the substrate entering the active site of the enzyme;

3. alteration of the conformation of the enzyme by the formation of the complex so that the free passage of electrons between the enzyme and mediator is inhibited despite their being in close proximity to each other; or 4. the blockage of access between the enzyme and mediator by the formation of the complex, thus preventing electron transfer.

In a typical homogeneous assay, therefore, formation of the complex perturbs an electrochemical characteristic of the components of the solution. It is not necessary for a full voltammogram to be determined in measuring the electrochemical characteristic; it may be sufficient, for example, for an appropriate poised potential to be selected and readings of current taken at that point. The degree of perturbation can then be related to the amount of ligand present in the sample, from calibration data obtained with similar systems using known amounts of ligand.

Although the order of introduction of the components (a), (b) and, if present, (c) into the apparatus may not be critical, it is preferable that a complex is formed after introduction of the final one of components (a), (b) and, if present, (c) but not prior thereto. It is, however, also possible for there to be complex present before the final one of these components is added, in which case the final component will become complexed by displacing one component of the complex. It may be necessary to incubate these components for a period of time to allow the complexing reaction to approach equilibrium before components (d) and (e) are added. Addition of components (d) and (e) should not affect the complexing reaction, but these components must be present before measurements can be taken at the working electrode.

In a method of the invention employing the so-called "sandwich" technique, a multivalent ligand is insolubilised with a solid phase binding partner and reacted with a specific binding partner in component (b) carrying an enzyme label. Subsequent addition of components (d) and (e) will permit the activity of the label to be monitored electrochemically. Depending on the order of the complexing reactions the forward, fast forward, reverse and simultaneous variations are all possible according to the present invention. The solid phase binding partner may be prepared by any one of a number of conventional techniques for immobilising reagents onto solid supports.

In a method of the invention exploiting the time (t) parameter, the rate of perturbation of the electrochemical characteristic as a result of complex formation may be determined. Conveniently, the initial rate of perturbation will be measured. Such a method is applicable, for example, to a competitive homogeneous assay in which the ligand and an enzyme-labelled ligand analogue compete for complexing with the specific binding partner. Thus, the initial rate of perturbation is related to the concentration of ligand present and from a calibration plot of the initial rate of perturbation v. concentration of ligand present, the ligand assay can be readily determined.

The method of assay involving a determination of the rate of perturbation is also applicable to non-competitive homogeneous assays where the enzyme-labelled ligand analogue is absent and sufficient labelled specific binding partner is employed to enable all the ligand introduced to be complexed.

In both homogeneous and heterogeneous assays, measurement of, for example, the absolute electrochemical current generated after a standard incubation period may enhance the ease and sensitivity of the assay.

In a typical heterogeneous assay, formation of the complex causes no (or only a slight) perturbation in an electrochemical characteristic of the components. In that case, it is necessary artificially to generate or enhance a perturbation by means of a controlled external influence. The magnitude of the external influence may have some bearing on the change induced, and must therefore be consistent with any such influence employed in calibration experiments, it is thought that any change produced in the perturbation remains a function of the ligand/specific binding partner complex.

The artificial generation or enhancement of the perturbation can be performed by displacement of the complex relative to the unbound enzyme-labelled component, for example by providing component (b) in an insolubilised form coupled (e.g. in conventional manner) to a solid support, with subsequent electrochemical measurement of either the free or bound enzyme label. Alternatively, the complex can be further complexed with a species which will bind specifically to the complex, coupled to a solid support, with subsequent displacement of the support and coupled molecules. In extreme cases, the displacement may constitute complete removal of the complex from the apparatus, but in general the complex will be displaced within the apparatus.

The solid support may be magnetic or magnetisable to facilitate displacement or separation. Thus, for example, magnetic supports (e.g. in the form of particles or beads) may be composed of ferromagnetic or paramagnetic materials such as metals (e.g. iron, nickel or cobalt), metal alloys (e.g. magnetic alloys of aluminium, nickel, cobalt and copper), metal oxides (e.g. $Fe_3O_4$, $\gamma$-$Fe_2O_3$, $CrO_2$, $CoO$, $NiO$ or $Mn_2O_3$), magnetoplumbites or solid solutions (e.g. solid solutions of magnetite with ferric oxide). The preferred material for magnetic supports is magnetite ($Fe_3O_4$) or haematite ($\gamma$-$Fe_2O_3$). Particles may be non-colloidal or colloidal (e.g. of the type described in our copending British Patent Application No. 8500092).

Displacement of the solid support, may, for example, be effected by urging the support into the vicinity of the electrode. In the case of magnetic supports (e.g. particles) the methods described in our copending British Patent Application No. 8417538 may suitably be employed. Thus, for example, a magnetic electrode (e.g. comprising a permanent magnet or an electromagnet) may be used, or a non-magnetic electrode may be used in which case the particles will be urged into and retained in the vicinity of the electrode by the application of an external magnetic field.

The component (b) may be immobilised directly on to the magnetic support, or may be immobilised via one or more other 'spacer' molecules, including partners in specific binding interactions. Immobilisation of reagents may generally be achieved by conventional techniques such as, for example, adsorption, covalent bonding or cross-linking, or a combination of these techniques, e.g. adsorption of a chemical with one or more functional groups followed by covalent bonding or cross-linking of the reagent. Alternatively, substantially non-chemical means may be employed suitable immobilisation techniques are known in the art.

Other methods for artificially generating or enhancing the perturbation include, for example, removing excess uncomplexed labelled reagent, e.g. by draining from the apparatus or by coupling to a suitable solid support and removing the said solid support from the apparatus.

All of the variations described above for homogeneous assays (including direct, competitive, sandwich and displacement techniques and methods in which a rate of perturbation is measured rather than an absolute perturbation) are equally applicable to heterogeneous assays.

The methods of the present invention are generally simpler than known methods, in that they allow direct monitoring of the enzyme label, and may eliminate the need for separation of uncomplexed and complexed phases before the assaying step.

If electrode-immobilised components are employed, the technique is further simplified in that the need for separate addition of the components to the electrochemical apparatus is eliminated. Additionally, the direct interaction between the electrode and the electrode-immobilised species may lead to an improvement in the sensitivity of the perturbation measurements.

According to a further feature of the present invention, therefore, there are provided methods of assay of a ligand in a sample as hereinbefore defined wherein one or more of the components (b), (c) and (e) is immobilised on the working electrode. The immobilised component(s) may be bound to the working surface of the electrode, or to a portion of the electrode other than the working surface.

Immobilised component (b) or (c) may for example be an immobilised specific binding partner (e.g. a capture antibody for use in sandwich immunoassay). Where component (b) or (c) is immobilised on an electrode, conventional techniques may be employed for immobilisation. It is essential, however, that immobilisation does not adversely affect the specific binding characteristics of the component. Where electrode-immobilised component (e) is employed, this may be an immobilised electron-transfer mediator or, electron-transfer promoter. Thus, for example, a polyviologen may be covalently bonded to a metal electrode. The large polyviologen molecule projects from the electrode surface and this is believed to facilitate interaction with the enzyme. Alternatively, chloranil and/or fluoranil may be disseminated throughout an electrode composed of particulate carbon.

If desired, more than one of components (b), (c) and (e) may be immobilised on the working electrode. In this case, each component may be directly bound to the electrode or one component may be bound via another component. For example, component (b) or (c) may be bound via component (e), as in the case where an enzyme-labelled specific binding partner is bound either via the enzyme or non-enzyme portion to an electrode-immobilised electron transfer mediator.

A preferred system comprises an electrode, e.g. a carbon (for example pyrolytic graphite) electrode, carrying an immobilised layer of ferrocene or a ferrocene derivative (e.g. 1,1'-ferrocene dicarboxylic acid, 1,1'-dimethyl ferrocene (DMF) or polyvinylferrocene having an average molecular weight of about 16000) which may interact in a bonding or non-bonding manner with the enzyme in the labelled component. The carbon electrode core can be integral or a stiff paste of particles. Normally, it will present a smooth surface for the ferrocene or ferrocene derivative, which may be adhered thereto in a number of ways, for example:

(a) for monomeric ferrocene or a monomeric ferrocene derivative, by deposition from a solution in a readily evaporatable liquid e.g. an organic solvent such as toluene;

(b) for a ferrocene polymeric derivative, e.g. polyvinyl ferrocene of average molecular weight about 16000 (for a method of synthesis see J. Polymer Sci. 1976, 14, 2433), deposition from a readily evaporatable organic solvent for the polymer such as chloroform;

(c) for a polymerisable ferrocene-type monomer, by electrochemically induced polymerisation in situ, e.g. by dissolving vinylferrocene in an organic electrolyte containing tertiary butyl ammonium perchlorate in concentration about 1M and depositing at a potential of $-700$ mV to induce deposition of vinylferrocene radicals as a polymer in situ; or (d) by covalent modification of the carbon electrode e.g. by carbodiimide cross-linking of the ferrocene or ferrocene derivative onto the carbon.

If desired, the electrode-immobilised component may be bound to a portion of the electrode other than the working surface. The electrode may in these circumstances be constructed so as to ensure that the immobilised component remains sufficiently close to the working surface to enable the assay to be carried out effectively. Such as electrode is illustrated in vertical cross-section in FIG. 2(a) of the accompanying drawings, this being particularly suitable for "sandwich" immunoassays in which the immobilised component is an unlabelled specific binding partner (e.g. a capture antibody). The electrode of FIG. 2(a) comprises an upwardly facing graphite working surface 1 in the base of a cell, the wall of which is formed by a polystyrene projection 2 from the body of the electrode. It is on this wall that a suitable specific binding partner may be immobilised (e.g. by adsorption). The electrical connection is provided by an insulated wire 3 secured to the bottom of the working surface by silver-loaded epoxy resin 4, the arrangement being encased in epoxy resin 5 and sealed with polypropylene 6.

It will be appreciated that, when component (b) is electrode-immobilised, it is not possible artificially to generate or enhance a perturbation by displacement of the resulting complex. However, a perturbation may still be artificially generated or enhanced, for example by complexing any uncomplexed enzyme-labelled component remaining in solution with a species which will complex specifically with that component, coupled to a solid support, with subsequent displacement of the support and coupled molecules.

In a further aspect, the present invention provides kits of reagents and apparatus for carrying out the assays of the invention. Suitable kits may comprise an electrochemical apparatus containing a working electrode, an auxiliary electrode and optionally a reference electrode, and an aqueous assay medium with suitable components present (either in solution or immobilised on the working electrode). Other components (e.g. further reagents etc) and the sample to be assayed may conveniently be introduced through an entry port provided in the apparatus.

The apparatus may be automated so that the components are added in a predetermined sequence, and the incubation temperature is controlled. Advantageously the apparatus may be pre-calibrated and provided with a scale whereby the perturbation in the electrochemical characteristic of the components may be ready off directly as an amount of ligand in the sample. Examples of ligands which may be assayed by the method of the invention are given in Table I below, together with an indication of a suitable specific binding partner in each instance.

TABLE I

| Ligand | Specific Binding Partner |
| --- | --- |
| antigen | specific antibody |
| antibody | antigen |
| hormone | hormone receptor |
| hormone receptor | hormone |
| polynucleotide strand | complementary polynucleotide strand |
| avidin | biotin |
| biotin | avidin |
| protein A | immunoglobulin |
| immunoglobulin | protein A |
| enzyme | enzyme cofactor (substrate) |
| enzyme cofactor (substrate) | enzyme |
| lectins | specific carbohydrate |
| specific carbohydrate of lectins | lectins |

The method of the invention has very broad applicability, but in particular may be used to assay: hormones, including peptide hormones (e.g. thyroid stimulting hormone (TSH), lutenising hormone (LH), follicle stimulating hormones (FSH) human chorionic gonadotrophin (HCG), insulin and prolactin) or non-peptide hormones (e.g. steroid hormones such as cortisol, estradiol, progesterone and testosterone and thyroid hormones such as thyroxine (T4) and triiodothyronine), proteins (e.g., carcinoembryonic antigen (CEA) and alphafetoprotein (AFP)), drugs (e.g. digoxin), sugars, toxins or vitamins.

The invention will be particularly described hereinafter with reference to an antibody or an antigen as the ligand; however, the invention is not to be taken as being limited to assays of antibodies or antigens.

It will be understood that the term "antibody" used herein includes within its scope a) any of the various classes or sub-classes of immunoglobulin, e.g. IgG, IgM, derived from any of the animals conventionally used, e.g. sheep, rabbits, goats or mice,
b) monoclonal antibodies,
c) intact molecules or "fragments" of antibodies, monoclonal or polyclonal, the fragments being those which contain the binding region of the antibody, i.e. fragments devoid of the Fc portion (e.g., Fab, Fab', F(ab')$_2$) or the so-called "half-molecule" fragments obtained by reductive cleavage of the disulphide bonds connecting the heavy chain components in the intact antibody.

The method of preparation of fragments of antibodies is well known in the art and will not be described herein.

The term "antigen" as used herein will be understood to include both permanently antigenic species (for example, proteins, bacteria, bacteria fragments, cells, cell fragments and viruses) and haptens which may be rendered antigenic under suitable conditions.

Techniques for labelling of an antibody with an enzyme are well known in the art (see, for example Ishakawa, Journal of Immunoassay 4, (1983) 209–327) and will not be discussed in detail herein. For example, the preparation of a conjugate of glucose oxidase with antibody to human AFP is described by Maiolini R. et al (J. Immunol. Methods 8, 223–234 (1975). Another method of labelling antibodies with glucose oxidase is described in "Protides of the Biological Fluids" Proc 24th Colloquium Brugge (Peeters H. ed) 1976, pp 787–784.

The labelled antibody may be purified before use, by methods which are known in the art. For example, the use of Sephadex G-200 for purifying glucose oxidase labelled IgG is described in the J. Immunol. Methods reference supra.

Methods for labelling an antigen are also known in the art. A review of such methods is to be found in Clinica Chimica Acta 81 pp 1–40 (1977) at p 4. Methods of purifying the labelled antigen are also known and include, for example, dialysis, density-gradient ultracentrifugation, gel filtration on Sephadex G-25 or G-200 and ion-exchange chromatography on DEAE-Sephadex.

The attachment of the label to the antibody or antigen can be via any portions of the molecular structures of the enzyme and the antibody or antigen, so long as catalytic activity of the former and immunological activity of the latter is retained.

Attachment of antibodies or antigens and enzyme-labelled versions of these reagents to the working electrode may be effected by conventional methods for immobilising antibodies, antigens or enzymes onto solid supports. Similarly, where it is desired artificially to generate or enhance a perturbation by displacement of reagents on solid (optionally magnetic) supports, or to effect separation in heterogeneous assay techniques using solid (optionally magnetic) supports, conventional methods for immobilising these reagents may be employed. Immobilisation may be via the antigen/antibody or, when present, the enzyme portion of the reagent.

The labelled reagent may, if desired, be immobilised on the electrode via the component (e). Alternatively, the labelled reagent may, if desired, be immobilised on the electrode separately from an immobilised component (e).

The component (e) may for example be conjugated via the label or the reagent portion of the labelled reagent. The component (e) which interacts with the label may be electrode-immobilised or in solution and, if the former, may be immobilised on the electrode before or after conjugation with the labelled reagent.

Incorporation of component (e) into the molecular structure of an antibody may where required be achieved, for example in the case of ferrocene, by any of the following methods:

(i) providing the ferrocene with one or more functional groups capable of bonding interactions with the molecular structure of the antibody;
(ii) using cross-linking groups;
(iii) using an avidin-biotin binding system, (i.e. avidin-carrying antibody binding with biotin-carrying ferrocene molecules or biotin-carrying antibody binding with avidin-carrying ferrocene);
(iv) using an antibody conjugated with a reagent (e.g. fluorescein isothiocyanate (FITC)) binding with a second antibody raised to the reagent (e.g. anti-FITC antibody) to which is coupled ferrocene;
(v) using a second antibody labelled with ferrocene, said second antibody being raised to the first antibody.

Similar methods may be applied as desired for the incorporation of ferrocene into an antigen molecule. Suitable methods are known in the art and will not be discussed in detail here. For example, the incorporation of ferrocene into certain steroids is described in Journal of Organometallic Chemistry, 160 (1978) pp. 223–230.

Thus, for example, antigens or antibodies can be assayed by competitive or direct, homogeneous or heterogeneous methods according to the invention. These methods are generally analogous to methods known in the art in which the enzyme label is monitored indirectly. In the method of the present invention, however, the activity of the enzyme is monitored by measurement of the desired electrochemical characteristic at the working electrode with reference to calibration data.

The method of the present invention provides many advantages over known assay methods employing enzymes. Without wishing to be bound by theoretical considerations, we believe that inter alia each of the following novel features of the present assay method may contribute to these advantages:

1. The use of a chemical species capable of aiding the transfer of electrons both to and from an electrode, as appropriate;
2. The measurement of a perturbation in the transfer of electrons due to complex formation;
3. The measurement of a perturbation in the transfer of electrons due to controlled external influences;
4. The use of an electron transfer mediator to aid the transfer of electrons;
5. The use of an electrode-immobilised electron transfer promoter to aid the transfer of electrons;
6. The use of an electrode-immobilised cofactor of an apoenzyme label to aid the transfer of electrons;
7. The measurement of a rate of perturbation in the transfer of electrons;
8. Any of the above features when applied to assays wherein one or more of the reagents are immobilised on the working electrode and more specifically, when applied to assays of an antigen ligand, any of the above features wherein an antibody is immobilised on the working electrode; and 9. Any of the above features when applied to immunoassays of antigens or antibodies.

By way of example only, the invention includes inter alia the following embodiments (it will be appreciated that, whilst the following embodiments illustrate assays in which electrons flow from a substrate to the electrode via the enzyme, analogous embodiments may also be achieved according to the invention, in which electrons flow from the electrode to the substrate via the enzyme, permitting reduction of the substrate):

1. Direct Homogeneous Antibody Assay:

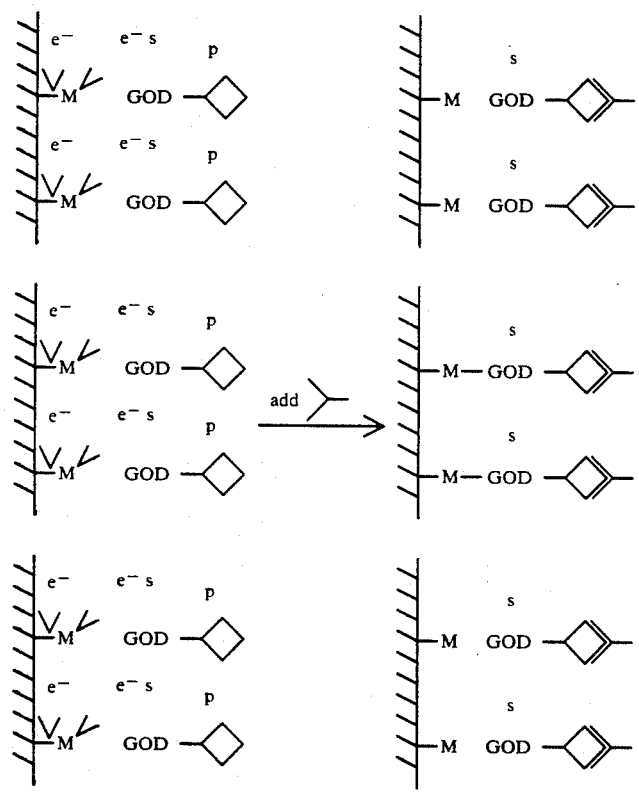

Figure 9:
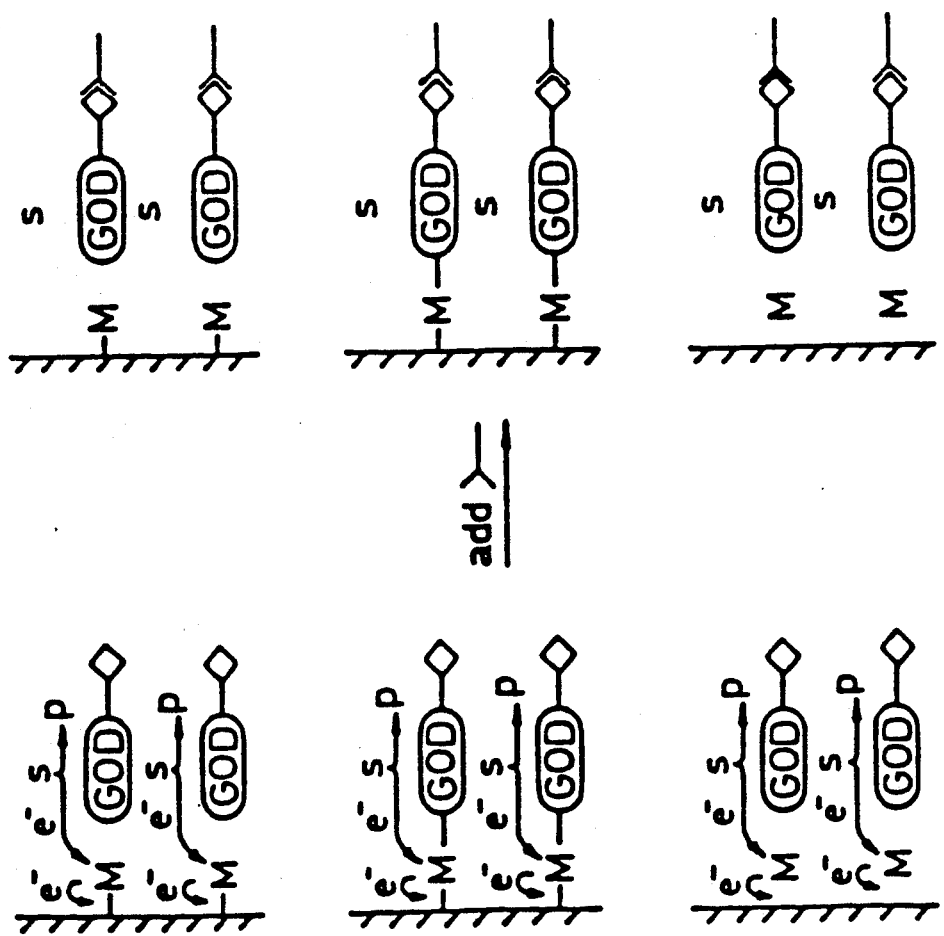
FIG. 9 is an illustration of a direct homogeneous antibody assay.

This type of assay is shown in FIG. 9.

The electrochemical activity of antigen labelled glucose oxidase (Ag-GOD) is monitored electrochemically. Addition of antibody (Ab) to the system results in the formation of the Ab-Ag-GOD complex. This partially or totally inhibits the activity of the Ag-GOD perturbing the electrochemical characteristics of the apparatus, the amount of perturbation being a measure of Ab concentration.

Figure 10:
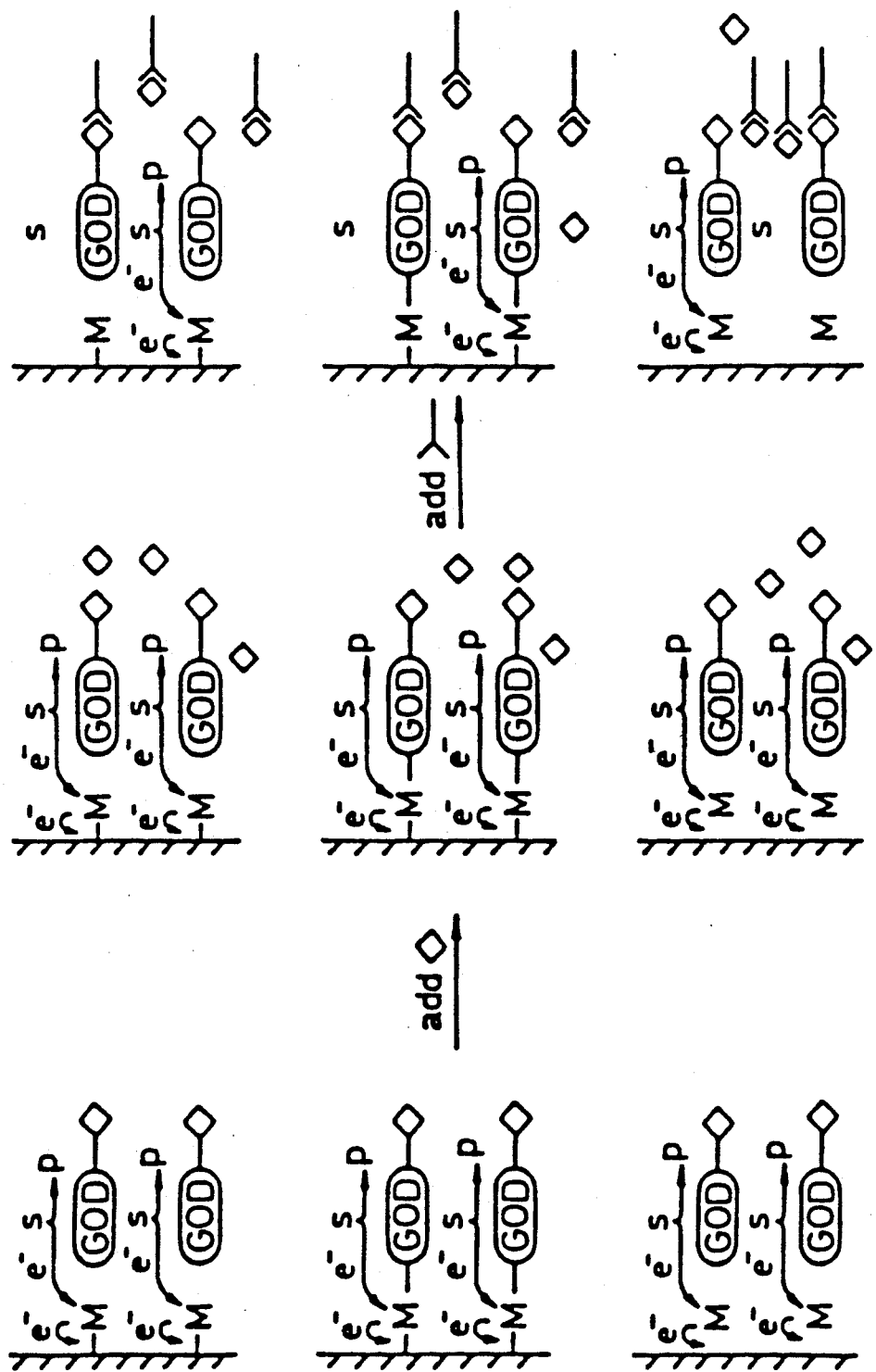
FIG. 10 is an illustration of a competitive homogeneous antigen assay.

2. Competitive Homogeneous Antigen Assay:

This type of assay is shown in FIG. 10.

Antigen (Ag) can be assayed competitively by adding the Ag sample to the Ag-GOD reagent and then adding a known concentration of Ab, competition between the Ag-GOD and Ag for the Ab results in some of the Ag-GOD being inhibited on Ab binding thus perturbing the electrochemical signal.

Figure 11:
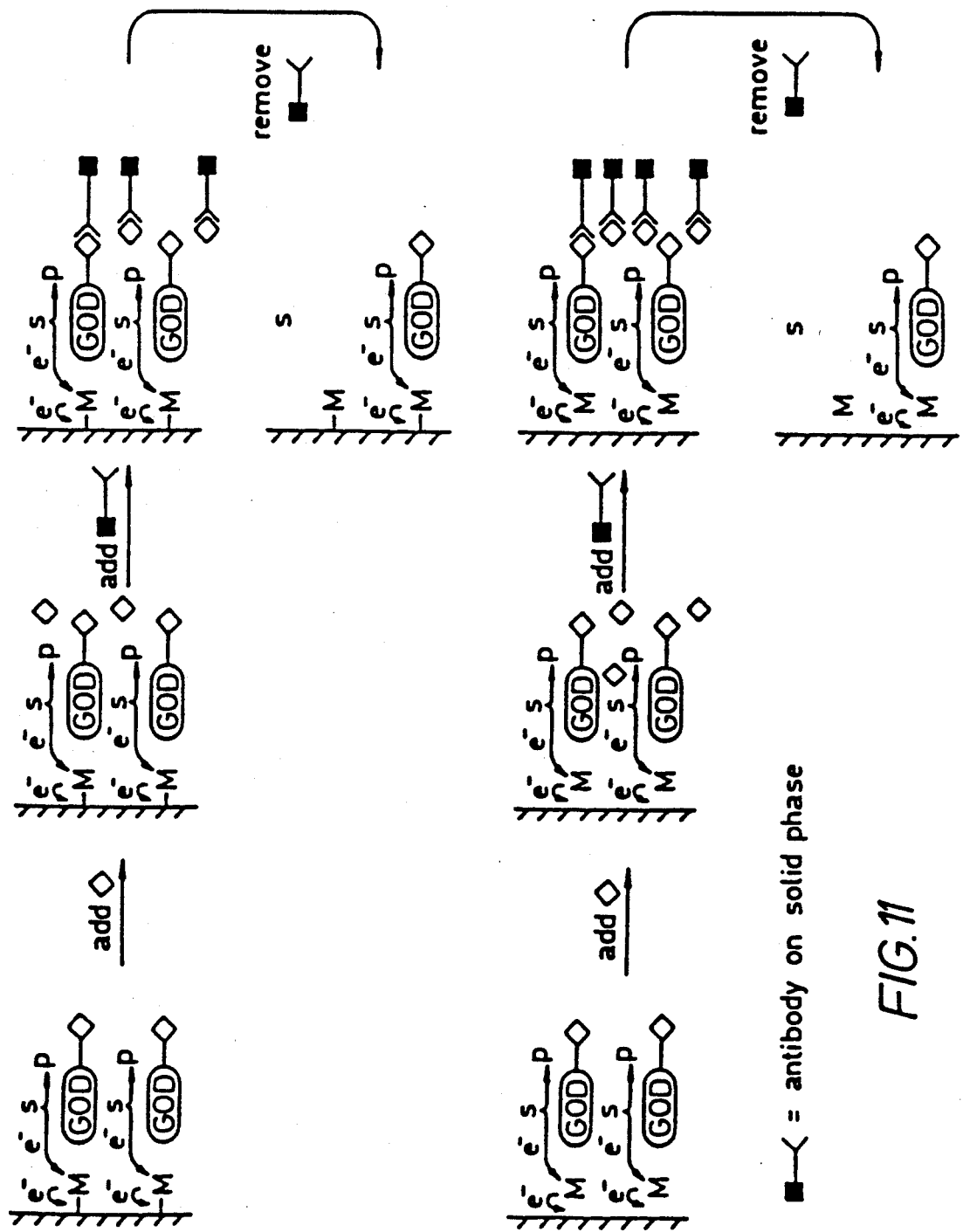
FIG. 11 is an illustration of a competitive heterogeneous antigen assay.

3. Competitive Heterogeneous Antigen Assay:

This type of assay is shown in FIG. 11.

Sample Ag is added to the electrochemical apparatus containing Ag-GOD without altering the electrochemical signal. Ab attached to solid phase is added which competes for Ag and Ag-GOD. Removal of the solid phase removes some of the Ag-GOD from the apparatus thus perturbing the electrochemical signal.

Figure 12:
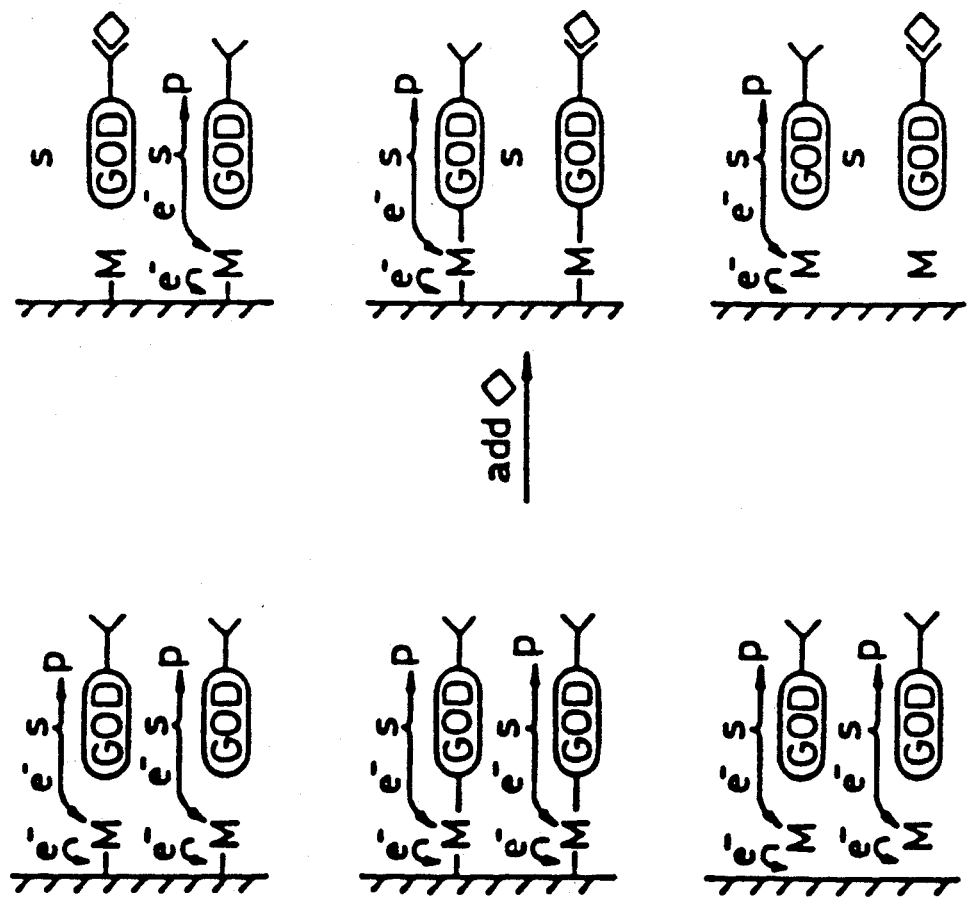
FIG. 12 is an illustration of a direct homogeneous antigen assay.

4. Direct Homogeneous Antigen Assay:

This type of assay is shown in FIG. 12.

The electrochemical activity of enzyme-labelled antibody (Ab-GOD) is monitored. Addition of the Ag sample inhibits the GOD perturbing the electrochemical signal. This assay may be carried out using a labelled antibody in solution or immobilised on the electrode.

Figure 13:
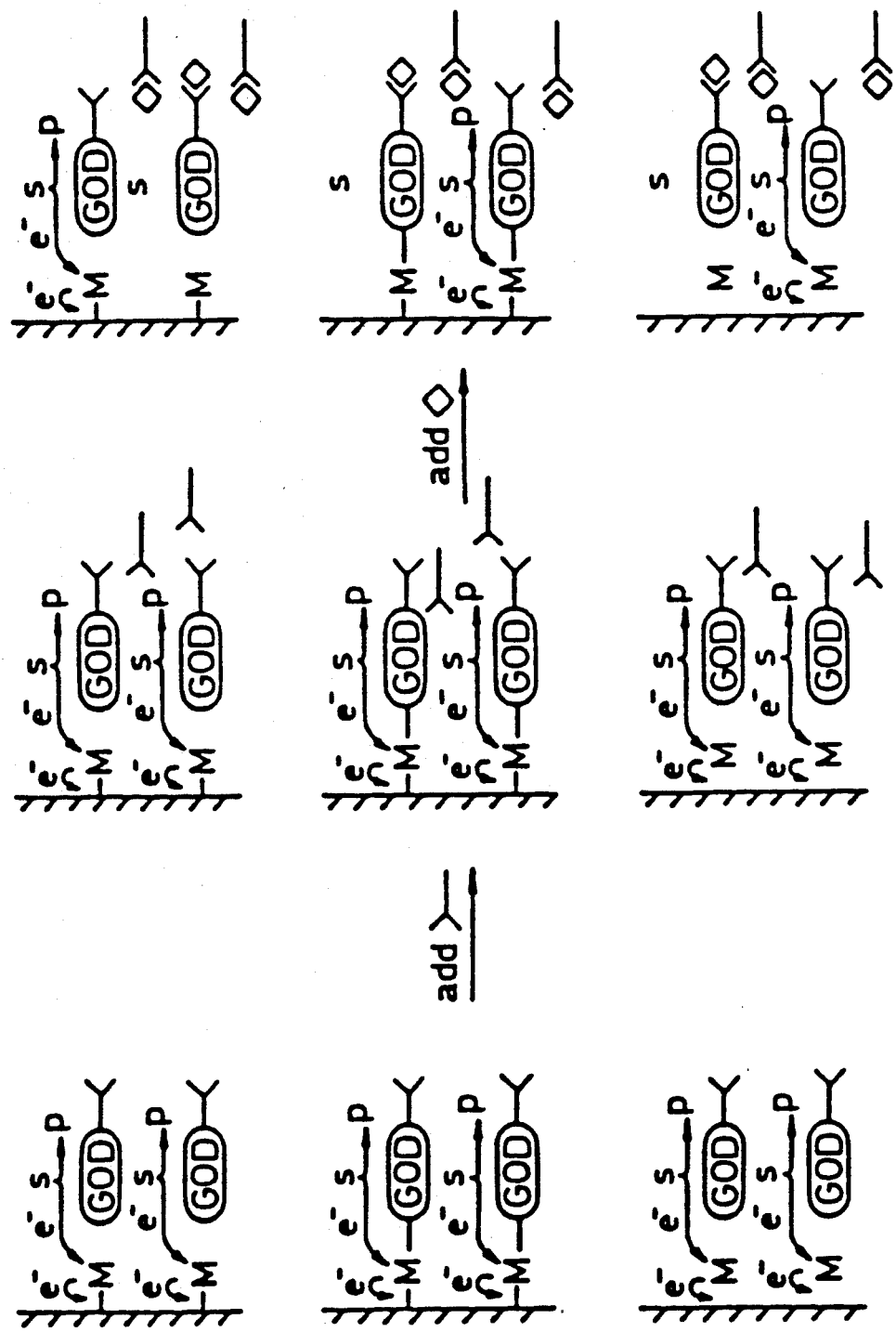
FIG. 13 is an illustration of a competitive homogenous antibody assay.

5. Competitive Homogeneous Antibody Assay:

This type of assay is shown in FIG. 13.

The electrochemical behaviour of Ab-GOD is monitored and then the sample Ab is added. Addition of a known amount of Ag takes place, the Ab and Ab-GOD, competing for the Ag. As some Ab binds to the Ab-GOD the electrochemical signal is perturbed.

Figure 14:
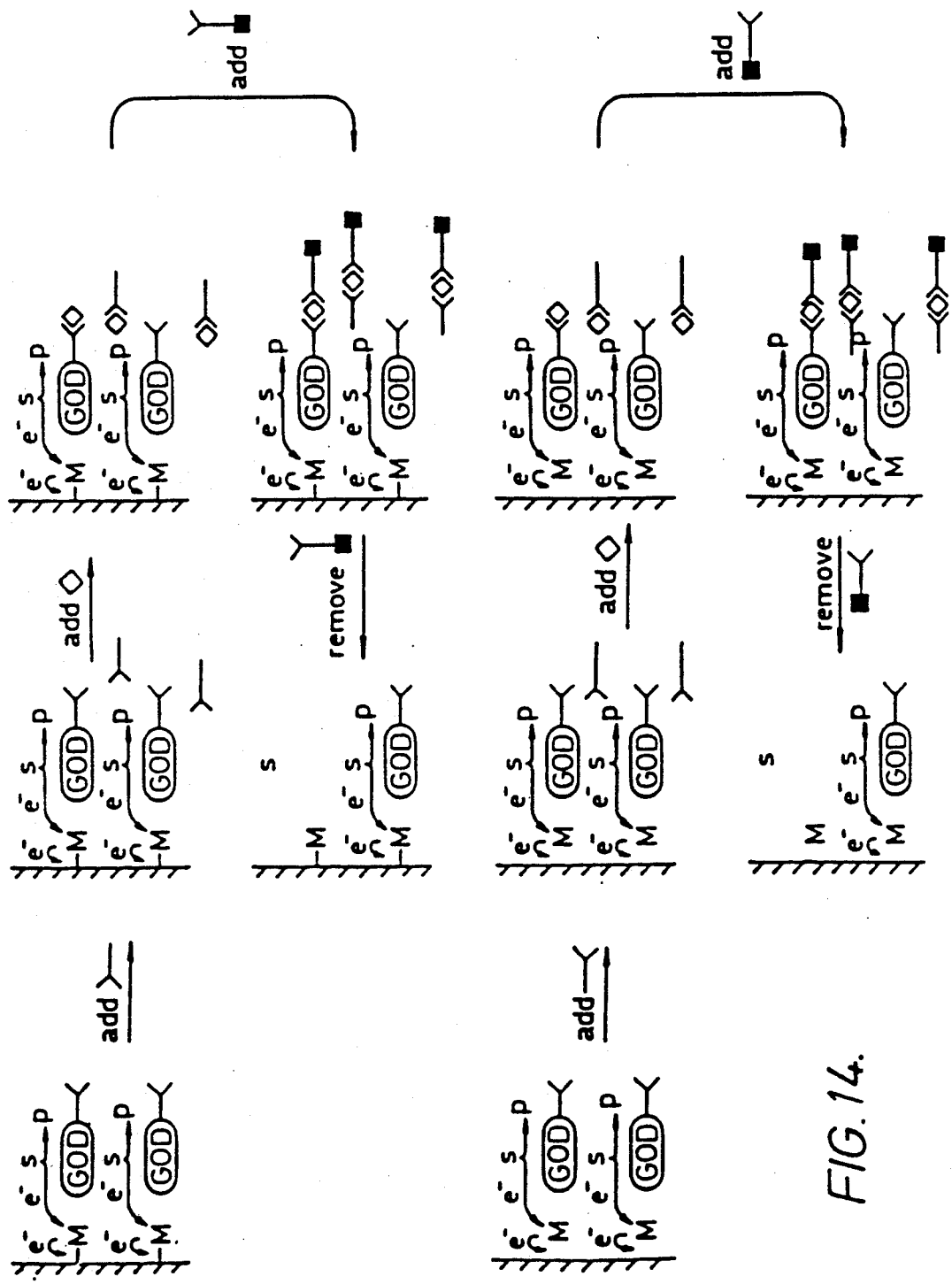
FIG. 14 is an illustration of a competitive heterogeneous antibody assay.

6. Competitive Heterogeneous Antibody Assay:

This type of assay is shown in FIG. 14.

The electrochemical activity of Ab-GOD is monitored and then the sample Ab added. Addition of a known volume of Ag is added, followed by Ab or solid phase. Removal of Ab on solid phase removes some of the Ab-GOD from the system perturbing the electrochemical signal.

The following non-limiting Examples are included as further illustration of the present invention:

EXAMPLE 1

ASSAY OF THYROXINE (T4) USING AN ENZYME-MODIFIED ANTIGEN ANALOGUE IN A COMPETITIVE HOMOGENEOUS ASSAY

In this assay, free enzyme-modified antigen is measured after competition between modified and unmodified antigen for a fixed number of antibody binding sites.

Preparation of Starting Materials (i) Coupling of Thyroxine (T4) to Glucose Oxidase: Preparation of modified glucose oxidase 1. Preparation of methyl thyroxinate hydrochloride Dried methanol was prepared by distilling methanol from magnesium, and stored over activated molecular sieve 3Å. Molecular sieve can be activated at 250°–300° C. The dry methanol was then saturated with HCl gas.

Thyroxine (1 g) was dissolved in the methanol/HCl, to which molecular sieve was added, and the mixture was left at room temperature overnight. The ester precipitates out with a yield of above 90%. After filtration, the product was washed with acetone and stored in a vacuum desiccator until use.

2. Preparation of the succinic anhydride derivative (product 2)

300 mg of methyl thyroxinate hydrochloride and 500 mg succinic anhydride was dissolved in 9 ml THF/DMF (50/50 v/v) to which was added 0.6 ml triethylamine. After reacting for 30 minutes the product was precipitated out with excess distilled water and filtered out of solution. The product was dissolved in acetone, filtered and then precipitated out with hexane.

THF = tetrahydrofuran
DMF = dimethylformamide

3. Coupling of Product 2 to Glucose Oxidase

Dry THF (4 ml) was cooled to −5° C. and product 2 (10 mg) was added with stirring. Triethylamine (15 μl) and isobutylchloroformate (13 μl) were added, the mixture was kept dry and at −5° C., with stirring for 30 minutes. The reaction mixture was then allowed to warm up to room temperature and stirred for a further 60 minutes. Glucose oxidase (110 mg) was dissolved up in 50 ml of 0.1M sodium bicarbonate solution. The THF solution was added dropwise with stirring to the glucose oxidase solution. The final solution was stirred for 24 hours at room temperature, then 5 ml 1M glycine solution was added and the solution stirred for a further hour. The solution was then spun to remove all solid matter, flavin (FAD) was added and the solution dialysed against water and 20 mM Tris/HCl pH 7.5 containing 0.1M NaCl. The solution was then concentrated to a suitable volume, filtered and applied to a gel filtration column (S-200) using the same buffer.

(ii) Preparation and Purification of Anti-Thyroxine Antibody

Anti-thyroxine antibody was a conventional polyclonal antiserum obtained by immunising sheep with thyroxine conjugated to a high molecular weight protein. To 10 ml of the antiserum was added 1.8 mg sodium sulphate and the mixture rolled for 30 minutes at room temperature. After centrifugation (1600 g for 30 minutes at room temperature) the supernatant was discarded and the precipitate redissolved in 10 ml water and the above procedure repeated. The antibody was then purified on a gel filtration column (G-25) pre-equilibrated with 10 mM Tris/HCl buffer, pH 7.4.

(iii) Preparation of Thyroxine Standard Solutions

Thyroxine (sodium salt) was obtained from Sigma London Chemical Company, England. Standard solutions were made by dissolving the thyroxine in sodium hydroxide (0.1M) and then diluting with Tris-HCl buffer (10 mM pH 7.4) to the desired concentration.

(iv) Apparatus to Measure the Electrochemistry of the Thyroxine-glucose Oxidase Analogue Cyclic voltammetry was performed in a three electrode electrochemical cell using a pyrolytic graphite working electrode. The Apparatus was the same as that shown in FIGS. 1(a) and 1(b) of the accompanying drawings.

(v) Detection of T4

Figure 3:
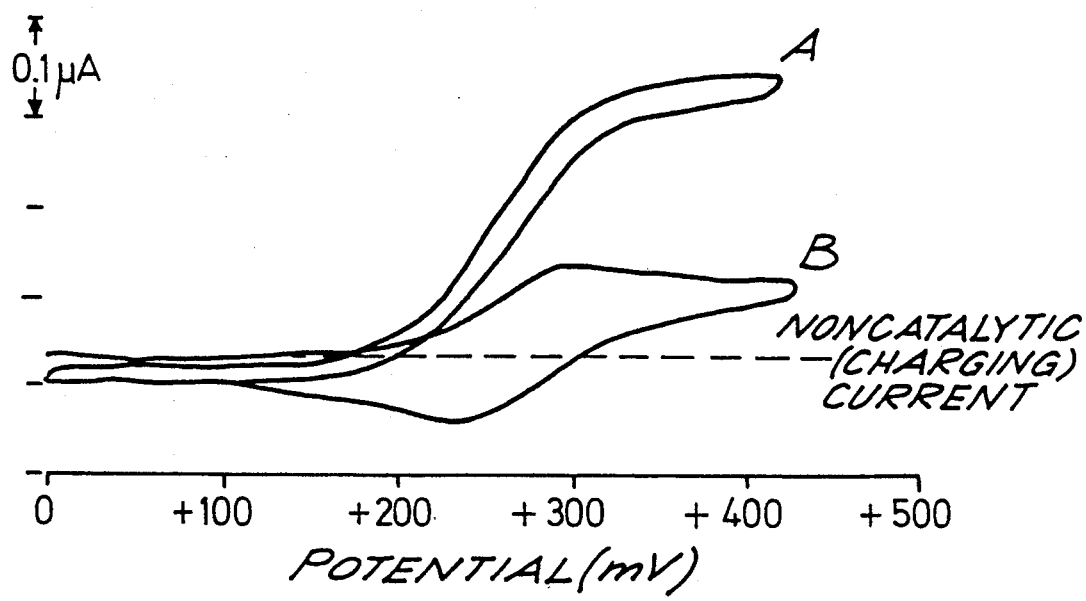
FIG. 3 is a voltammogram of ferrocene monocarboxylic acid as described in Example 1.
Figure 3:
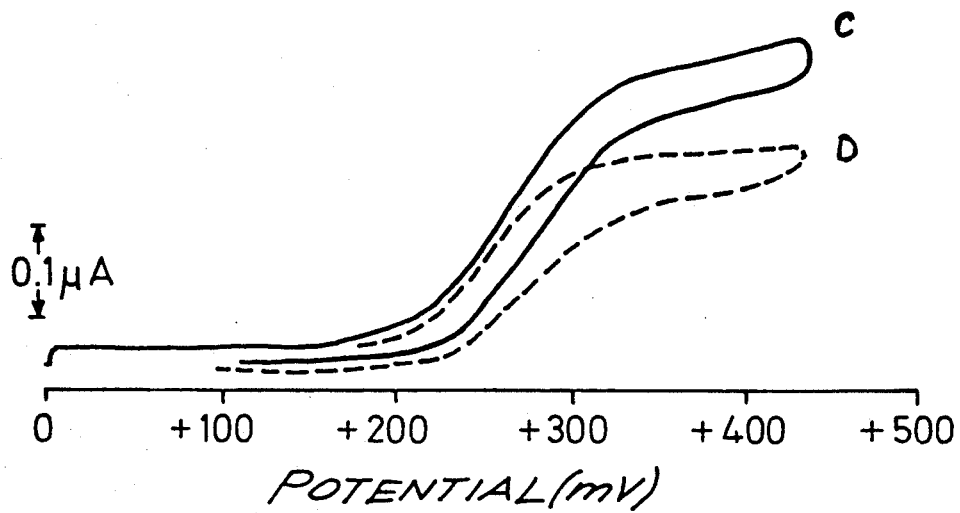

The electrochemistry of glucose oxidase labelled thyroxine (T4-GOD) at a pyrolytic graphite electrode was studied in the presence and absence of anti-T4 antibody, ferrocene monocarboxylic acid (FMCA) acting as the electron transfer mediator. Increasing concentrations of T4-GOD in Tris-HCl buffer (50 mM; pH 7.5) were incubated for 30 minutes in the presence or absence of antibody at 20° C. After 30 minutes β-D glucose (final concentration being 100 mM) and FMCA (final concentration being 10 mM) were added and a cyclic voltammogram between 0 and +500 mV was produced (scan rate of 2mV s$^{-1}$). The current recorded at potential of +300 mV was measured, this corresponding to a peak in current in the cylic voltammogram of FMCA—see FIG. 3. All values of current were corrected for the uncatalytic background (charging) current. Curve A shows the cyclic voltammogram of glucose oxidase+FMCA+glucose; curve B shows the cyclic voltammogram of FMCA+glucose; curve C shows the cyclic voltammogram of T4-GOD (102.5 ng T4 ml$^{-1}$)+FMCA+glucose+buffer; and curve D shows the cyclic voltammogram of T4-GOD (102.5 ng T4 ml$^{-1}$)+FMCA+glucose+buffer+anti-T4 antibody.

(vi) Assay Procedure for Thyroxine

Duplicate samples were run in which 10 μl of thyroxine standard was added to 10 μl of the thyroxine-glucose oxidase analogue (2.3×10$^{-5}$M) and mixed in the electrochemical cell after which 100 μl of the anti-thyroxine antibody was added. After mixing, the reagents were incubated for 30 minutes at 37° C., 50 μl of electron transfer mediator (ferrocene monocarboxylic acid 6.0 mM in 10 mM Tris/HCl buffer, pH 7.4), 50 μl of enzyme substrate (β-D-glucose (molar) containing 100 mM magnesium chloride) and 280 μl of buffer (10 mM Tris/HCl pH 7.4) were added. After allowing the reagents to come to thermal equilibrium, a cyclic voltammogram was made from 0 to +450 mV versus a standard calomel electrode (voltage scan rate=5 mV per second). The peak current was measured and the electrochemical signal calculated.

Figure 4:
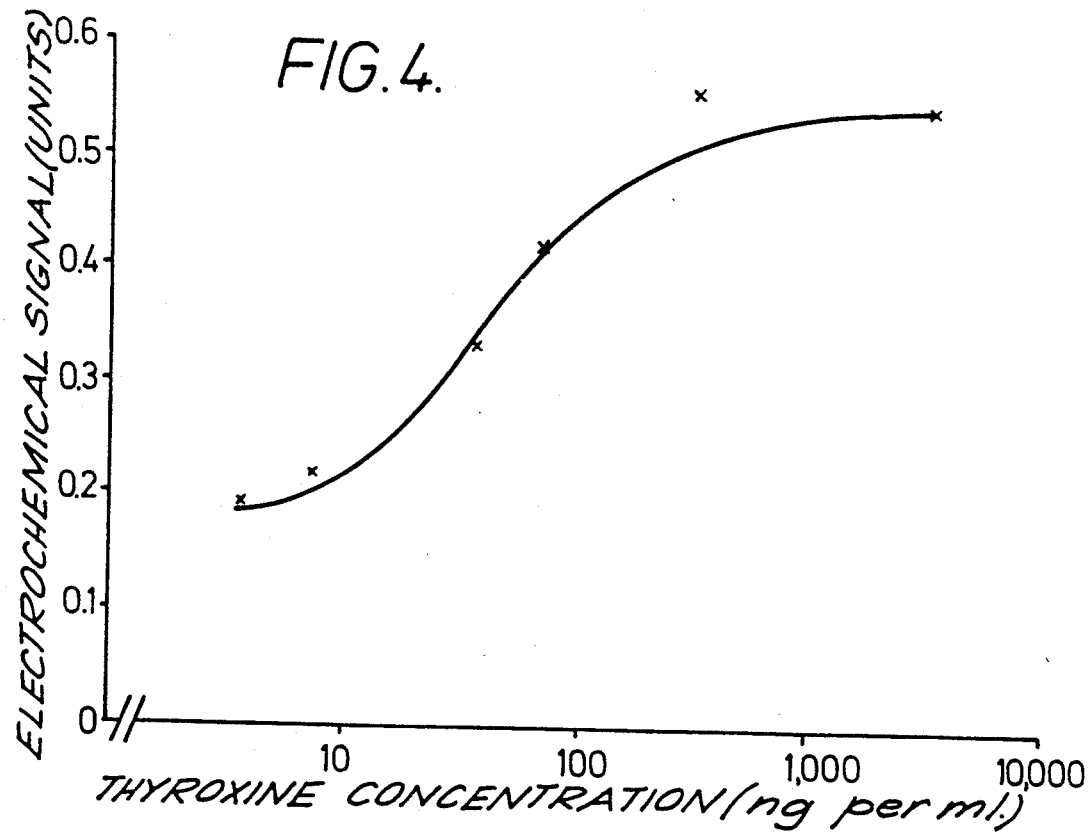
FIG. 4 is a graph of electrochemical signal versus concentration as described in Example 1.

The electrochemical signal is defined as:

$$\text{signal} = \frac{i - i_o}{i_o}$$

where $i$ = peak electrochemical current for the sample
$i_o$ = peak electrochemical -continued
current for the zero standard An example electrochemical signal versus thyroxine concentration curve is shown in FIG. 4. The electrochemical signal (in arbitrary units) is plotted on the vertical axis whilst thyroxine concentration in nanograms per milliliter is plotted along the horizontal axis.

EXAMPLE 2

ASSAY OF HUMAN CHORIONIC GONADOTROPHIN (hCG) USING AN ENZYME MODIFIED ANTIBODY WITH ENHANCEMENT OF PERTURBATION USING CONTROLLED EXTERNAL INFLUENCES

Preparation of Starting Materials (i) Enzyme Modified Anti-hCG Monoclonal Antibodies Monoclonal antibodies were obtained from mouse ascites fluid by the process reported by Milstein and Kohler in Nature 256 495–497 (1975). Antibodies from individual hybridoma cell lines were screened to identify those producing antibody to discrete antigenic determinants. Those having the highest affinities to hCG were selected for use in the assay.

To 6 mg of antibody A (in 2 ml of sodium phosphate buffer, 100 mM pH 7.4) 200 $\mu$l of $\beta$-mercaptoethylamine (100 mM) and ethylenediaminetetraacetic acid, disodium salt (10 mM) in water, were added. The mixture was incubated at 37° C. for 90 minutes and the antibody was desalted on a gel filtration column (TSK 3000 SW) pre-equilibrated in phosphate buffer.

14 mg of glucose oxidase was dissolved in 1.3 ml of phosphate buffer to which 20 $\mu$l of a 15 mg solution of succinimidyl 4-(N-maleimide-methyl) cyclohexane-1-carboxylate (SMCC) in dioxan was added whilst stirring. 20 $\mu$l aliquots of SMCC were added at 5 minute intervals until a total of 180 $\mu$l of SMCC in dioxan was added and, after the reaction had been allowed to proceed at 30° C. for two hours, the solution was desalted on a gel filtration column (G-25) preequilibrated in phosphate buffer (100 mM, pH 7.0 containing 100 mM EDTA).

Equimolar ratios of enzyme and antibody were mixed and rolled at 4° C. under argon for 68 hours. The enzyme/antibody conjugate was then purified by gel filtration yielding a product incorporating 1 enzyme molecule per antibody molecule. The fractions which showed both high enzyme and immunological activities were retained and used in the assay.

(ii) Preparation of Anti-hCG (Antibody B) Conjugated to Fluorescein Isothiocyanate (FITC)

A second monoclonal antibody to hCG (antibody B) specific for a different antigenic determinant was conjugated to FITC.

Conjugation of FITC to monoclonal antibody was achieved by reacting 200 $\mu$g fluorescein isothiocyanate (FITC) Sigma London Chemical Co., England with 5 mg antibody in 1.4 ml sodium bicarbonate buffer, 0.2M, pH 9.0, for 18 hours at room temperature. The reaction mixture was purified by gel filtration on Sephadex G-50 superfine, giving a product incorporating an average of 6 molecules FITC per antibody molecule.

(iii) Preparation of Anti-FITC Antibody Covalently Coupled to Magnetisable Solid Phase Anti-FITC was a conventional polyclonal antiserum obtained by immunising sheep with FITC conjugated to keyhole limpet haemocyanin. The magnetisable cellulose particles were a composite of cellulose containing approximately 50% black ferric(ous) oxide ($Fe_3O_4$), with mean particle diameter of 3 microns (see Forrest and Rattle, "Magnetic Particle Radioimmunoassay" in Immunoassays for Clinical Chemistry, p 147–162, Ed Hunter and Corrie, Churchill Livingstone, Edinburgh (1983)). Anti-FITC antiserum was covalently coupled to the magnetisable cellulose following cyanogen bromide activation of the cellulose, according to the procedure of Axen et al, Nature 214, 1302–1304 (1967). The antiserum was coupled at a ratio of 2 ml antiserum to 1 gram of magnetisable solid phase.

Anti-FITC magnetisable solid phase was diluted to 10 mg per ml in Tris-HCl buffer (10 mM per liter, pH 7.4).

(iv) Preparation of hCG Standard Solutions

A freeze dried preparation of hCG, calibrated against the first international reference preparation (75/537) was obtained from Biodata SpA, Milan, Italy. This sample was diluted in buffer (Tris-HCl, (10 mM, pH 7.4) to the desired concentration.

(v) Apparatus Used for Electrochemical Measurement

The electrochemical apparatus was the same equipment as that of Example 1.

(vi) Assay Procedure for hCG

An immunometric immunoassay using glucose oxidase modified anti-hCG monoclonal antibody was used to measure hCG.

Duplicate samples were run in which 50 $\mu$l of hCG standard was mixed with 50 $\mu$l antibody A (9.4 $\mu$g protein per ml) and 50 $\mu$l of antibody B (6 $\mu$g protein per ml). After mixing, the samples were incubated at room temperature for 30 minutes, 100 $\mu$l of anti-FITC magnetisable solid phase was added and, after vigorous mixing, was incubated for 5 minutes, also at room temperature. The application of an external magnetic field permitted the separation of bound and free components, the solid phase being retained and the supernatant discarded. After two washes with 250 $\mu$l of distilled water, the solid phase was resuspended in buffer (100 $\mu$l of 10 mM Tris/HCl, pH 7.4) and added to the electrochemical cell which contained electron transfer mediator (40 $\mu$l of ferrocene monocarboxylic acid (FMCA) 6.7 mM in 10 mM Tris/HCl, pH 7.4), enzyme substrate (40 $\mu$l of molar glucose solution containing 100 mM magnesium chloride) and 170 $\mu$l of Tris/HCl buffer (10 mM, pH 7.4). The application of an external magnetic field to the working electrode by contacting it with a permanent magnet caused the magnetic solid phase to be concentrated on the electrode surface. Once the solid phase had been concentrated at the working electrode surface and reached thermal equilibrium (temperature $T = 37 \pm 1°$ C.), the electrochemical current due to the bound glucose oxidase activity was measured by making a cyclic voltammogram from +120 mV to +420 mV versus a standard calomel electrode (voltage scan rate = 2 mV per second).

Figure 5:
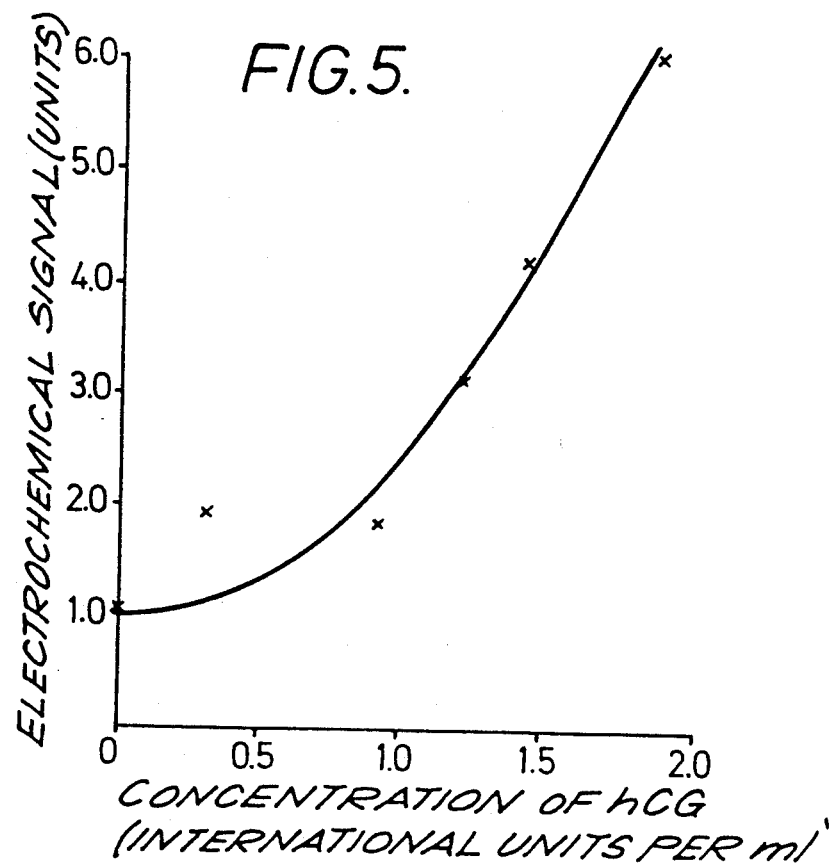
FIG. 5 is a graph of electrochemical signal versus concentration as described in Example 2.

A plot of electrochemical signal versus hCG concentration is shown in FIG. 5. The electrochemical signal is defined as signal =

$$\frac{\text{peak current for sample} - \text{peak } FMCA \text{ background current}}{\text{peak current for zero} - \text{peak } FMCA \text{ background current}}$$

The electrochemical signal (in arbitrary units) is plotted on the vertical axis whilst the hCG concentration (in International units per milliliter) is plotted on the horizontal axis.

EXAMPLE 3

ASSAY OF HUMAN CHORIONIC GONADOTROPHIN (hCG) USING AN ENZYME MODIFIED ANTIBODY WITH ENHANCEMENT OF PERTURBATION USING CONTROLLED EXTERNAL INFLUENCES

Preparation of Starting Materials (i) Enzyme Modified Anti-hCG Monoclonal Antibodies:

The method was the same as that in Example 2.

(ii) Preparation of Anti-hCG (Antibody B) Conjugated to Fluorescein Isothiocyanate (FITC)

The method employed was the same as that in Example 2.

(iii) Preparation of Anti-FITC Antibody Covalently Coupled to Magnetisable Solid Phase For method see Example 2.

(iv) Preparation of hCG Standard Solutions

The method was the same as that in Example 2.

(v) Apparatus Used for Electrochemical Measurement:

The electrochemical apparatus was the same equipment as that of Example 1.

Assay Procedure for hCG

An immunometric immunoassay using glucose oxidase modified anti-hCG monoclonal antibody was used to measure hCG.

Duplicate samples were run in which 50 μl of hCG standard was mixed with 50 μl antibody A (10 μg protein per ml) and 50 μl of antibody B (6 μg protein per ml). After mixing, the samples were incubated at room temperature for 30 minutes. 100 μl of anti-FITC was added and, after vigorous mixing, was incubated for 5 minutes, also at room temperature. The application of an external magnetic field permitted the separation of bound and free components, the solid phase being retained and the supernatant discarded. The retained solid phase was washed three times with 200 μl of 10 mM Tris/HCl buffer, pH 7.4 containing 0.9% w/v sodium chloride before being resuspended in 100 μl 10 mM Tris/HCl buffer, pH 7.4. The solid phase was transferred to the electrochemical cell which contained electron transfer mediator (40 μl of dimethylaminomethyl ferrocene 0.6 mM in 10 mM Tris/HCl, pH 7.4), enzyme substrate (40 μl of molar glucose containing 100 mM magnesium chloride) and 170 μl of Tris/HCl buffer (10 mM pH 7.4). The application of an external magnetic field to the working electrode by contacting it with a permanent magnet caused the magnetic solid phase to be concentrated on the electrode surface. Once the solid phase had been concentrated at the electrode surface and reached thermal equilibrium (assay temperature = 37±1° C.), the electrochemical current due to the bound glucose oxidase activity was measured by making a cyclic voltammogram from 0 to +500 mV versus a standard calomel electrode (voltage scan rate = 5 mVs$^{-1}$).

Figure 6:
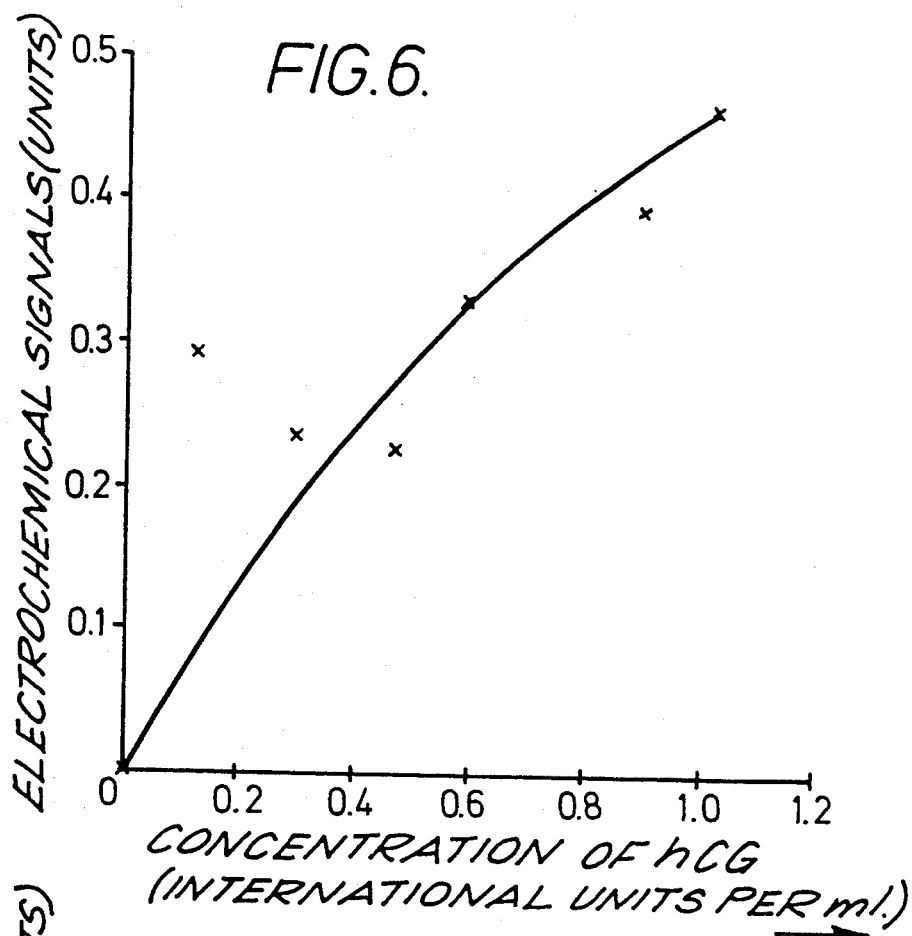
FIG. 6 is a graph of electrochemical signal versus concentration as described in Example 3.

A plot of electrochemical signal versus hCG concentration is shown in FIG. 6. The electrochemical signal is defined as $$\text{signal} = \frac{i - i_o}{i_o}$$

where $i$ = peak current for sample—peak mediator current $i_o$ = peak current for zero sample—peak mediator current.

The electrochemical signal (in arbitrary units) is plotted on the vertical axis whilst hCG concentration (in International Units per milliliter) is plotted along the horizontal axis.

EXAMPLE 4

SANDWICH ASSAY OF HUMAN CHORIONIC GONADOTROPHIN (hCG) USING AN ELECTRODE-IMMOBILISED CAPTURE ANTIBODY AND AN ENZYME MODIFIED SECOND ANTIBODY

Preparation of Starting Materials (i) Enzyme Modified Anti-hCG Monoclonal Antibodies The method of preparation described in Example 2 was used (Antibody A).

(ii) Structure of Working Electrode

Figure 2A:
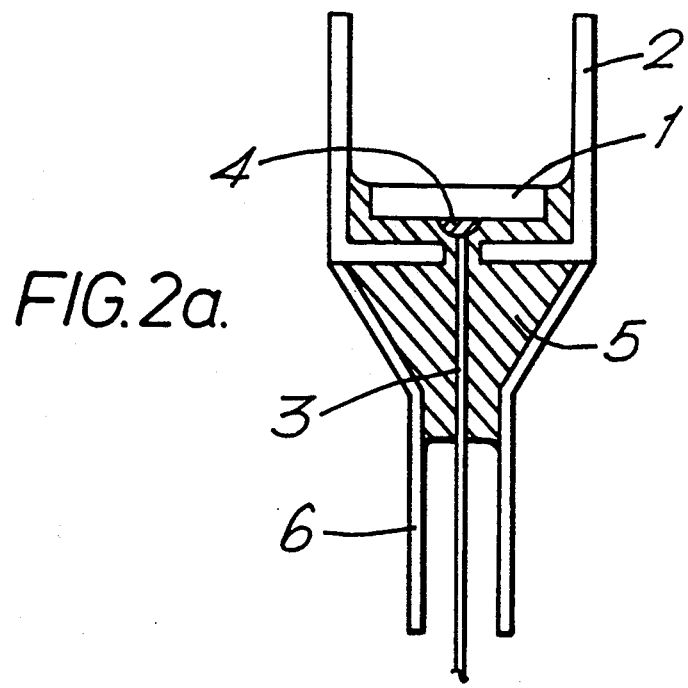
FIG. 2 shows a vertical cross section of an electrode which can be used in the instant invention.
FIG. 2b shows a circuit in which the electrode of FIG. 2a can be used.

A modified electrode of the type shown in FIG. 2a was constructed as follows:

An insulated wire was attached to a 4 mm diameter disc of pyrolytic graphite with silver loaded epoxy resin. The disc was then fixed into the bottom of a polystyrene microtitration well (Nunc Intermed) with epoxy resin. A length of polypropylene tubing was then attached to the bottom of the polystyrene wall to act as a handle.

(iii) Electrode Immobilised Capture Antibody

A second monoclonal antibody (antibody B in Example 2) was immobilised onto the wall of the modified working electrode as follows:

Antibody B was diluted in Tris/HCl buffer (10 mM, pH 7.4) to a concentration of 33.9 μg per ml; 330 μl of this solution was added to the electrode well and left for 1 hour at room temperature for the antibody to adsorb onto the electrode wall. The electrode was then washed 10 times with Tris/HCl buffer and then 300 μl of a solution of ovalbumin (5 mg per ml in 10 mM Tris/HCl pH 7.4 containing 0.1% v/v Nonidet P40 detergent) for 1 hour to block any free sites for protein adsorption on the electrode walls. After further washes in Tris/HCl buffer (10 mM, pH 7.4), the electrode surface was polished with an alumina/water slurry (alumina particles 0.3 μm diameter) before use.

(iv) Preparation of hCG Standard Solutions

See Example 2 for details.

(v) Apparatus Used for Electrochemical Measurements

Figure 2B:
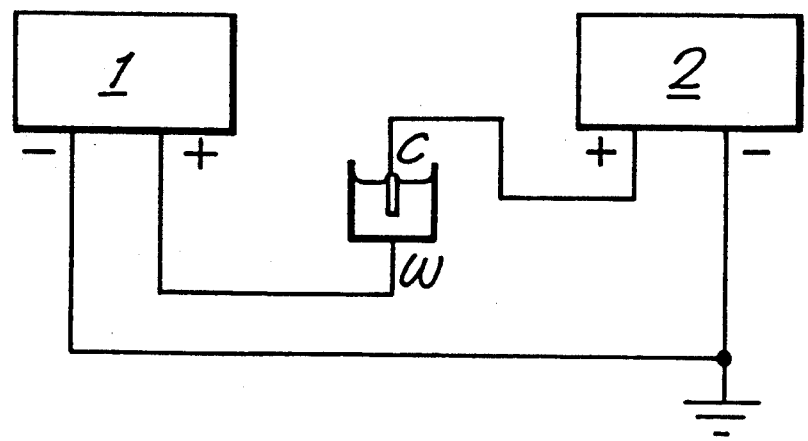

A two-electrode system was employed in these measurements, the previously described working electrode being used in conjunction with a platinum counter-electrode. The arrangement is illustrated in FIG. 2b of the accompanying drawings. The working electrode W, which forms the cell, containing the assay medium, is connected to the positive terminal of a Voltage Scan Generator 1 (the negative terminal being grounded); the platinum counter-electrode C is connected to the positive terminal of a sensitive current meter 2, the other terminal of which is also grounded.

(vi) Assay Procedure for hCG

An immunometric immunoassay using glucose oxidase modified anti-hCG monoclonal antibody was used to measure hCG.

100 μl of hCG standard and 100 μl of antibody A were added to the well of the working electrode. After mixing, the sample was incubated at room temperature for 30 minutes. The reagents were poured out of the working electrode well and the electrode was washed 3 times with 350 μl of Tris/HCl (10 mM, pH 7.4 containing 0.9% w/v sodium chloride). After polishing the graphite surface with alumina slurry, 160 μl buffer (10 mM Tris/HCl, pH 7.4), 20 μl electron transfer mediator (0.6 mM dimethylaminomethyl ferrocene in Tris/HCl (10 mM, pH 7.4) and 20 μl substrate (molar glucose solution containing 100 mM magnesium chloride) were added to the electrode well and degassed with argon. A cyclic voltammogram from 0 to +650 mV was made (voltage scan rate=5 mVs$^{-1}$) and the peak currents calculated.

After each measurement the electrode well was washed out with Tris/HCl buffer (10 mM, pH 7.4) and the 350 μl of 2M magnesium chloride was added to the cell. After 2 minutes the electrode well was emptied and rinsed with buffer to make ready for reuse.

Figure 7:
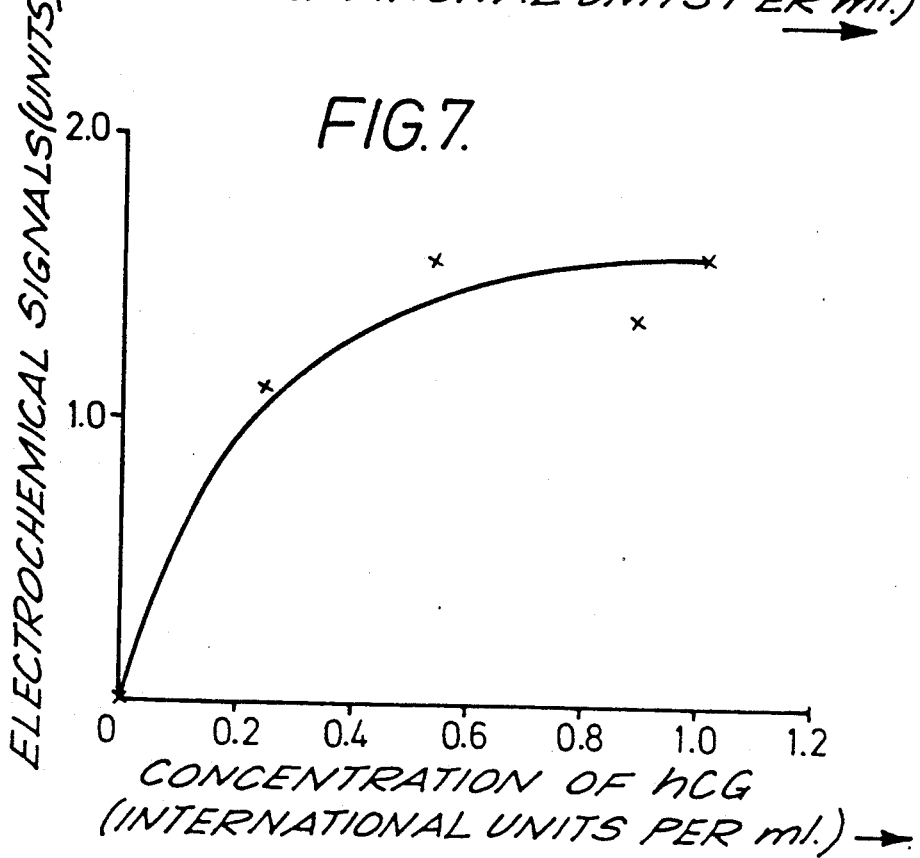
FIG. 7 is a graph of electrochemical signal versus concentration as described in Example 4.

FIG. 7 present the results of such an hCG assay The electrochemical signal is defined as $$\text{signal} = \frac{i - i_o}{i_o}$$

where i=peak sample current—peak mediator current
$i_o$=zero sample current—peak mediator current.

Electrochemical signal (arbitary units) is plotted on the vertical axis whilst hCG concentration (in International Units per ml) is plotted along the horizontal axis.

EXAMPLE 5

FURTHER ASSAY OF HUMAN CHORIONIC GONADOTROPIN (hCG) USING AN ELECTRODE-IMMOBILISED CAPTURE ANTIBODY AND AN ENZYME MODIFIED SECOND ANTIBODY

Preparation of Starting Materials (i) Enzyme Modified Anti-hCG Monoclonal Antibodies See Example 2.

(ii) Electrode-immobilised Capture Antibody

A second monoclonal antibody (antibody B in example 2) was immobilised onto the working surface of a pyrolytic graphite working electrode using the methods of Bourdillon et al (Journal of the American Chemical Society 102 (1980) 4231–4235) and Cass et al (Analytical Chemistry 56 (1984) 667–671). After polishing with an alumina/water slurry (particle diameter=0.3 μm) the electrode was oxidised electrochemically at +2.2 V versus a standard calomel electrode (S.C.E.) in 10% nitric acid containing 2.5% w/v potassium dichromate for 10 seconds and then placed in 0.63 ml of solution of 1-cyclohexyl-3-(2-morpholinoethyl) carbodiimide p-methyltoluenesulphonate (Sigma London Chemical Co., England) (0.15 molar in 0.1 molar acetate buffer, pH 4.5) for 80 minutes at 20° C. After washing with water, the electrode was soaked in acetate buffer (0.1 molar, pH 9.5) containing 0.49 mg per ml of antibody B for 90 minutes at 20° C. The electrode was washed with water and placed in a solution of ovalbumin (5 mg per ml in 10 mM Tris/HCl buffer, pH 7.4, containing 0.1% v/v Nonidet P40 detergent) for 90 minutes at 20° C. to block any remaining protein binding sites. After washing with water the electrode was stored in Tris/HCl buffer (10 mM pH 7.4) at 4° C. until use.

(iii) Preparation of hCG Standard Solutions
See Example 2.

(iv) Apparatus Used for Electrochemical Measurements
See Example 2.

Assay Procedure for hCG

An immunometric immunoassay using glucose oxidase modified anti-hCG monoclonal antibody was used.

The charging current of the electrode was determined in buffer (10 mM Tris/HCl pH 7.4) by running a cyclic voltammogram from 0 to +480 mV versus S.C.E. (voltage scan rate=5 mVs$^{-1}$; T =37±1° C.). 25 μl of hCG standard and 25 μl of antibody A were mixed and the electrode on which was immobilised the capture antibody, antibody B, was added; the electrode was incubated for 15 minutes at 20° C. The electrode was then washed with water, with buffer (10 mM Tris/HCl, pH 7.4 containing 0.9% w/v sodium chloride) then water before adding to the electrochemical cell which contained 400 μl buffer (10 mM Tris/HCl, pH 7.4), 50 μl of electron transfer mediator (0.3 mM dimethylaminomethyl ferrocene in 10 mM Tris/HCl buffer, pH 7.4) and 50 μl of substrate solution (molar glucose containing 100 mM magnesium chloride). After allowing the electrode to come to thermal equilibrium (T=37±1° C.), a cyclic voltammogram between 0 and +480 mV versus S.C.E. was calculated, the electrode charging current being subtracted from this value. The electrode was washed with water and then soaked in 2 molar magnesium chloride solution for 2 minutes to break the antibody/antigen bond. After washing once more with water, the electrode was ready for reuse.

Figure 8:
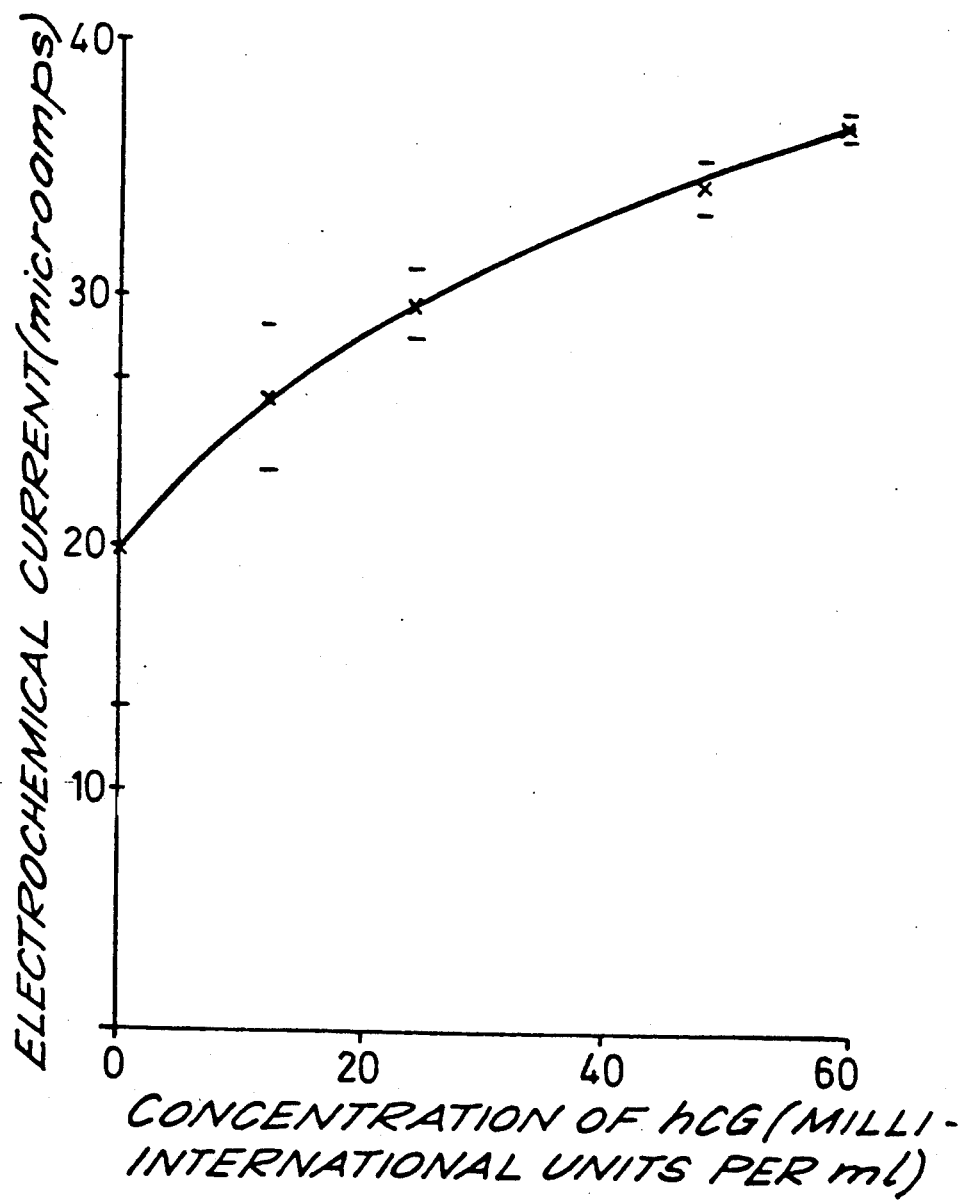
FIG. 8 is a graph of electrochemical current versus concentration as described in Example 5.

FIG. 8 presents the results of such an assay. The electrochemical signal (in microamps) is plotted on the vertical axis whilst the hCG concentration (in milli-international Units per ml) is plotted along the horizontal axis.

We claim:

1. In a homogeneous method of electrochemical assay of a ligand in a sample using an electrochemical apparatus having at least a working electrode and and auxiliary electrode and containing components comprising:
   (a) the sample,
   (b) a specific binding partner to the ligand and at least one further reagent selected from ligand analogues and specific binding partners to the ligand, one of the components (b) being labelled with an oxidoreductase enzyme, and
   (c) a substrate for the enzyme, the improvement which comprises said apparatus additionally containing an electron transfer chemical capable of aiding the transfer of electrons between the substrate and the working electrode via the enzyme as a result of oxidation or reduction of the substrate but which is not essential for the activity of said enzyme, and the method including the step of determining whether the said transfer of electrons is perturbed by formation of a complex of said ligand with at least one specific binding partner.

2. A method as claimed in claim 1, wherein said electron transfer chemical is an electron transfer mediator which accepts electrons from one of the enzyme and the working electrode and donates them to the other of the working electrode and enzyme.

3. A method as claimed in claim 1 wherein at least one of the components (b) and said electron transfer chemical is immobilised on the working electrode.

4. A method as claimed in claim 1 wherein said electron transfer chemical comprises an electron transfer mediator formed from ferrocene or a derivative thereof.

5. A method as claimed in claim 4, wherein the derivative of ferrocene contains at least one or more side chains of the formula $-CHO$, $-(CH_2)_nCOOH$ or $-(CH_2)_mNR^1R^2$ (where n and m are each from 0 to 6 and $R^1$ and $R^2$, which may be the same or different, each represents hydrogen or an alkyl group containing 1 to 4 carbon atoms).

6. A method as claimed in claim 1 wherein the perturbation in the transfer of electrons is determined from a perturbation in a peak current at a pre-selected constant potential of the working electrode relative to a reference electrode.

7. A method as claimed in claim 1, wherein the ligand is an antigen or an antibody.

8. A method as claimed in claim 1 wherein said electron transfer chemical is an electrode-immobilized electron transfer promoter which retains the enzyme in close proximity with the working electrode by being immobilized on said working electrode without taking up a charge during said electron transfer.

9. A method as claimed in claim 1, wherein the extent to which said transfer of electrons is perturbed is determined, the extent of perturbation being an indication of the amount of ligand in the sample.

10. A method as claimed in claim 4, wherein the extent to which said transfer of electrons is perturbed is determined, the extent of perturbation being an indication of the amount of ligand in the sample.

11. A method as claimed in claim 7, wherein the extent to which said transfer of electrons is perturbed is determined, the extent of perturbation being an indication of the amount of ligand in the sample.

12. A kit for carrying out a method of assay comprising in separate containers:
(i) at least one specific binding partner to the ligand or a specific binding partner to the ligand and at least one further reagent selected from ligand analogs and specific binding partners to the ligand, one of the components (i) being labelled with an oxidoreductase enzyme,
(ii) a substrate for the enzyme and
(iii) an electron transfer chemical capable of aiding the transfer of electrons between the substrate and an electrode via the enzyme as a result of oxidation or reduction of the substrate.

13. A kit as claimed in claim 12 which further comprises an electrochemical apparatus containing a working electrode and an auxiliary electrode.

14. In a heterogeneous method of electrochemical assay of a ligand in a sample using an electrochemical apparatus having at least a working electrode and an auxiliary electrode and containing components comprising:
(a) the sample
(b) a specific binding partner to the ligand or a specific binding partner to the ligand and at least one further reagent selected from ligand analogues and specific binding partners to the ligand, one of the components (b) being labelled with an oxidoreductase enzyme, and
(c) a substrate for the enzyme, the improvement which comprises said apparatus additionally containing an electron transfer chemical capable of aiding the transfer of electrons between the substrate and the working electrode via the enzyme as a result of oxidation or reduction of the substrate but which is not essential for the activity of said enzyme, and the method including the steps of providing means for separation of any enzyme-labelled complex containing said ligand relative to any other enzyme-labelled component, or where an enzyme-labelled ligand analog is present as component (b) providing means for separation of any complex containing said ligand analog relative to non-complexed enzyme-labelled ligand analog, and determining whether the said transfer of electrons is thereby perturbed.

15. A method as claimed in claim 14, wherein said electron transfer chemical is an electron transfer mediator which accepts electrons from one of the enzyme and the working electrode and donates them to the other of the working electrode and enzyme.

16. A method as claimed in claim 14 wherein at least one of the unlabelled ligand analog, unlabelled specific binding partner to the ligand and said electron transfer chemical is immobilised on the working electrode.

17. A method as claimed in claim 14 wherein said electron transfer chemical comprises an electron transfer mediator formed from ferrocene or a derivative thereof.

18. A method as claimed in claim 17, wherein the derivative of ferrocene contains at least one side chain of the formula $-CHO$, $-(CH_2)_nCOOH$ or $-(CH_2)_mNR^1R^2$ (where n and m are each from 0 to 6 and $R^1$ and $R^2$, which may be the same or different, each represents hydrogen or an alkyl group containing 1 to 4 carbon atoms).

19. A method as claimed in claim 14 wherein the perturbation in the transfer of electrons is determined from a perturbation in the peak current at a pre-selected constant potential of the working electrode relative to a reference electrode.

20. A method as claimed in claim 14, wherein the ligand is an antigen or an antibody.

21. A method as claimed in claim 14 wherein said electron transfer chemical is an electrode-immobilized electron transfer promoter which retains the enzyme in close proximity with the working electrode by being immobilised on said working electrode without taking up a charge during said electron transfer.

22. A method as claimed in claim 14, wherein the extent to which said transfer of electrons is perturbed is determined, the extent of perturbation being an indication of the amount of ligand in the sample.

* * * * *